(12) United States Patent
Wei et al.

(10) Patent No.: US 10,045,760 B2
(45) Date of Patent: Aug. 14, 2018

(54) SAMPLING DEVICE CAPABLE OF CONTINUOUSLY SAMPLING CONTENT IN A BIOLOGICAL CONDUIT AND METHOD THEREOF

(71) Applicants: Xibo Wei, Hayward, CA (US); Sara Shi Wei, Hayward, CA (US)

(72) Inventors: Xibo Wei, Hayward, CA (US); Sara Shi Wei, Hayward, CA (US)

(73) Assignees: Xibo Wei, Hayward, CA (US); Sara Wei, Hayward, CA (US)

( * ) Notice: Subject to any disclaimer, the term of this patent is extended or adjusted under 35 U.S.C. 154(b) by 0 days.

(21) Appl. No.: 15/486,606

(22) Filed: Apr. 13, 2017

(65) Prior Publication Data
US 2017/0215849 A1    Aug. 3, 2017

(51) Int. Cl.
| A61B 10/00 | (2006.01) |
| A61F 13/36 | (2006.01) |
| A61F 13/20 | (2006.01) |

(52) U.S. Cl.
CPC ........ *A61B 10/0038* (2013.01); *A61B 10/007* (2013.01); *A61B 10/0051* (2013.01); *A61F 13/2005* (2013.01); *A61F 13/2008* (2013.01); *A61F 13/2011* (2013.01); *A61F 13/2017* (2013.01); *A61F 13/36* (2013.01); *A61B 2010/0054* (2013.01); *A61B 2010/0061* (2013.01); *A61B 2010/0074* (2013.01); *A61B 2503/40* (2013.01); *A61B 2562/162* (2013.01); *A61F 2013/2014* (2013.01)

(58) Field of Classification Search
CPC ............ A61B 10/0038; A61B 10/0051; A61B 10/007; A61B 2010/0054; A61B 2010/0061; A61B 2010/0074
See application file for complete search history.

(56) References Cited

U.S. PATENT DOCUMENTS

| 5,971,942 A | 10/1999 | Gu et al. | |
| 7,449,001 B2 | 11/2008 | Stoltz | |
| 8,491,495 B1 | 7/2013 | Shuck | |
| 2005/0177069 A1* | 8/2005 | Takizawa | A61B 1/041 600/573 |
| 2008/0299005 A1* | 12/2008 | Meathrel | A61K 9/006 422/552 |
| 2009/0161100 A1* | 6/2009 | Minot | G02B 21/34 356/244 |
| 2017/0196488 A1* | 7/2017 | Hofius | A61B 5/1486 |

* cited by examiner

*Primary Examiner* — Jeffrey G Hoekstra
*Assistant Examiner* — Jonathan M Foreman
(74) *Attorney, Agent, or Firm* — Guosheng Wang; United States Research and Patent Firm

(57) ABSTRACT

The present invention provides a device that can move inside a biological conduit such as an intestinal tract for sampling the content therein, and a process thereof. While moving along the intestinal tract, the device can continuously collect the content in the intestinal tract. One or more convoy belts having an adsorbent layer are configured to continuously absorb and preserve the collected intestinal content. The belt loaded with the sample may be used to establish a chemical, biochemical and microbiological spectrum along the length of the intestinal tract.

15 Claims, 22 Drawing Sheets

SAMPLING DEVICE CAPABLE OF CONTINUOUSLY SAMPLING CONTENT IN A BIOLOGICAL CONDUIT AND METHOD THEREOF

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable

FIELD OF THE INVENTION

The present invention generally relates to a sampling device capable of continuously sampling the content in a biological conduit, and a method thereof. The conduit may be a biological conduit such as human or animal intestinal tract or gut, but it may also be an industrial conduit. Embodiments of this invention can advance the fields of intestinal endocrinology, endoscopy, and microbiology by extending the sampling device into sections of the intestinal tract and obtaining biochemical and microbe samples in conjunction with a sample gathering and handling system, data acquisition, and data analysis. Although the invention will be illustrated, explained and exemplified with a sampling device for the intestinal tract, it should be appreciated that the present invention can serve clinical diagnostic, treatment and research purposes in other fields, for example, biological conduit including gastrointestinal tract, respiratory tract, and the like.

BACKGROUND OF THE INVENTION

Many times, the content in a biological conduit needs to be sampled and analyzed. Take human or animal intestinal tract or gut as an example. Small intestine (AKA small bowel) is the part of the gastrointestinal tract between the stomach and the large intestine. The average length of the small intestine in a living person is about 6 meters. The small intestine does not only digest food and absorb nutrients and minerals, but also support the body's immune system. Jejunum is the midsection of the small intestine, connecting the duodenum to the ileum. It is about 2.5 m long, and contains the plicae circulares, and villi that increase its surface area. In the jejunum, digestion products such as sugars, amino acids, and fatty acids are absorbed into the bloodstream. The ileum is the final section of the small intestine, and is about 3 m long. The ileum absorbs mainly vitamin B12 and bile acids, as well as any other remaining nutrients. The ileum joins to the cecum of the large intestine at the ileocecal junction. Peyer's patches located within the ileum are an important part of the digestive tract's local immune system. These patches are part of the lymphatic system, and provide a site for antigens from potentially harmful bacteria or other microorganisms in the digestive tract to be sampled, and subsequently presented to the immune system. The jejunum and ileum are suspended in the abdominal cavity by mesentery. The mesentery is part of the peritoneum. Arteries, veins, lymph vessels and nerves travel within the mesentery.

Large intestine (AKA large bowel) includes many sections along its 1.5-meter length, such as cecum and appendix, ascending colon, transverse colon, descending colon, sigmoid colon, rectum, and anal canal. Lymphatic drainage from the ascending colon and proximal two-thirds of the transverse colon is to the colic lymph nodes and the superior mesenteric lymph nodes, which drain into the cisterna chyli. The lymph from the distal one-third of the transverse colon, the descending colon, the sigmoid colon, and the upper rectum drain into the inferior mesenteric and colic lymph nodes. The lower rectum to the anal canal above the pectinate line drain to the internal iliac nodes. The anal canal below the pectinate line drains into the superficial inguinal nodes.

Moreover, the immunological function of the intestinal tract is also associated with the complex community of microorganisms called gut flora or gut microbiota. For example, the large intestine houses over 700 species of bacteria that perform a variety of functions, as well as fungi, protozoa, and archaea. The amount of microbes in a human distal gut is in the vicinity of 100 trillion. In humans, the gut flora is established at one to two years after birth, and by that time, the intestinal epithelium and the intestinal mucosal barrier that it secretes have co-developed in a way that is tolerant to, and even supportive of, the gut flora and that also provides a barrier to pathogenic organisms. Some human gut microorganisms benefit the host by fermenting dietary fiber into short-chain fatty acids (SCFAs), such as acetic acid and butyric acid. Intestinal bacteria also play a role in synthesizing vitamin B and vitamin K as well as metabolizing bile acids, sterols, and xenobiotics. The systemic importance of the SCFAs and other compounds they produce are like hormones, and the gut flora itself appears to function like an endocrine organ. Dysregulation of the gut flora has been correlated with a host of inflammatory and autoimmune conditions.

People tend to underestimate the importance of gut flora, which plays many key roles. The gut flora community defends against pathogens by fully colonizing the space, making use of all available nutrients, and by secreting compounds that kill or inhibit unwelcome organisms that would compete for nutrients with it. It develops and maintains the intestinal epithelium and inducing antibody production. It helps to metabolize otherwise indigestible compounds in food. The gut flora may even train and develop the immune system.

Surprisingly, recent study shows that biochemical signaling can take place between the gastrointestinal tract and the central nervous system, via the so-called "gut-brain axis". The gut-brain axis includes the central nervous system, neuroendocrine and neuroimmune systems including the hypothalamic-pituitary-adrenal axis (HFA axis), sympathetic and parasympathetic arms of the autonomic nervous system including the enteric nervous system and the vagus nerve, and the gut microbiota. As a bidirectional neurohumoral communication system, the gut-brain axis is important for maintaining homeostasis and is regulated through the central and enteric nervous systems and the neural, endocrine, immune, and metabolic pathways. The gut flora can produce a range of neuroactive molecules, such as acetylcholine, catecholamines, γ-aminobutyric acid, histamine, melatonin, and serotonin, which is essential for regulating peristalsis and sensation in the gut. Changes in the composition of the gut flora due to diet, drugs, or disease correlate with changes in levels of circulating cytokines, some of which can affect brain function. Likewise, chronic or acutely stressful situations activate the hypothalamic-pituitary-adrenal axis, causing changes in the gut flora and intestinal epithelium, and possibly having systemic effects. Additionally, the cholinergic anti-inflammatory pathway, signaling through the vagus nerve, affects the gut epithelium and flora. Hunger and satiety are also integrated in the brain. There may be a relationship between the gut flora and anxiety disorders and mood disorders including depression; schizophrenia, autism, Parkinson's disease, and obsessive-compulsive disorder.

That being said, it is critically important to sample and study the content in an intestinal tract. However, the human gut is largely unexplored, except for post mortem autopsies, which do not reflect much of the most important living dynamic phenomena and conditions. Many diseases with origin in human gut are of unknown causes, so only symptoms are treated. For example, the remote and inaccessible 15' sections of intestines, beyond the 6 feet up and 6 feet down as viewed by endoscopy/colonoscopy instruments, remain unexplored in live humans. Even these upper and lower extremities that are viewed by camera can only be treated for visible damage, such as polyps or ulcers. A camera pill may be swallowed, and pictures are taken throughout the intestinal tract, but the information gleaned is largely qualitative. As such, quantitative in-vivo data and measurements are generally not available.

There is hence a serious need to analyze the biochemical, biological, physiological, and bioengineering processes taking place within the entire human intestinal tract, as precisely as in other anatomical systems (e.g. DNA, and microbiology). Advantageously, the present invention provides a sampling device capable of continuously sampling the content in human or animal intestinal tract, and a method thereof. The present invention enables an easy and convenient operation for collection and preservation of intestinal bio/chemical profile for external analysis, and measurements of many in vivo conditions. The invention can support medical professionals' decisions-making such as construction of mathematical, physiological, biochemical, and other engineering models; delineation of causes of diseases originating within the gut; and prescribing diets or medications.

SUMMARY OF THE INVENTION

One aspect of the present invention provides a sampling device that can entirely or partially enter into a conduit, and can move along the conduit for sampling a content contained therein. The device comprises a housing defining a chamber, and the chamber has a first opening (or inlet). A sample collector collects the content in the conduit. A collector driver drives the sample collector, and a sample delivery deliveries the sample collected by the sample collector to the collector driver.

In a representative embodiment, the present invention provides a sampling device that can entirely or partially enter into an intestinal tract, and can move along the intestinal tract for sampling a content contained therein. The device comprises a housing defining a chamber, and the chamber has a first opening (or inlet). A sample collector collects the content of the intestinal tract. A collector driver drives the sample collector, and a sample delivery deliveries the sample collected by the sample collector to the collector driver.

Another aspect of the invention provides a process of sampling content in a conduit using the sampling device as described above. The process includes the steps of:

inserting the sampling device entirely or partially into the conduit;

moving the sampling device along the conduit;

collecting the content of the conduit in the sample collector; and delivering the sample content collected by the sample collector to the collector driver.

In a representative embodiment, the invention provides a process of sampling content in an intestinal tract using the sampling device as described above. The process includes the steps of:

inserting the sampling device entirely or partially into the intestinal tract;

moving the sampling device along the intestinal tract;

collecting the content of the intestinal tract in the sample collector; and delivering the sample content collected by the sample collector to the collector driver.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

The term "conduit" is intended to include a biological conduit, an industrial conduit, or any combination thereof. Examples of the biological conduit include, but are not limited to, human or animal intestinal tract or gut, gastrointestinal tract, buccal cavity, pharynx, esophagus, stomach, small intestine, duodenum, jejunum, ileum, large intestine, cecum, colon, rectum, anal canal, respiratory tract, upper respiratory tract, lower respiratory tract, nasal cavity, paranasal sinuses, pharynx, nasopharynx, oropharynx, laryngopharynx, larynx, trachea, bronchi (primary, secondary and tertiary), bronchioles (including terminal and respiratory), lungs (including alveoli), ear canal, vagina, cervix, uterus or womb, Fallopian tubes, ovaries, urinary tract, kidney, renal pelvis, ureter, urinary bladder, and urethra etc. Examples of the industrial conduit include, but are not limited to, various tubular structures in an industrial apparatus, equipment, a product, a machine, a production line, and the like.

In the following description, the invention will be illustrated and described using intestinal tract as a representative example. However, it should be appreciated that the invention may be applied to any other conduit structures for sampling the content therein, mutatis mutandis.

Figure 1:
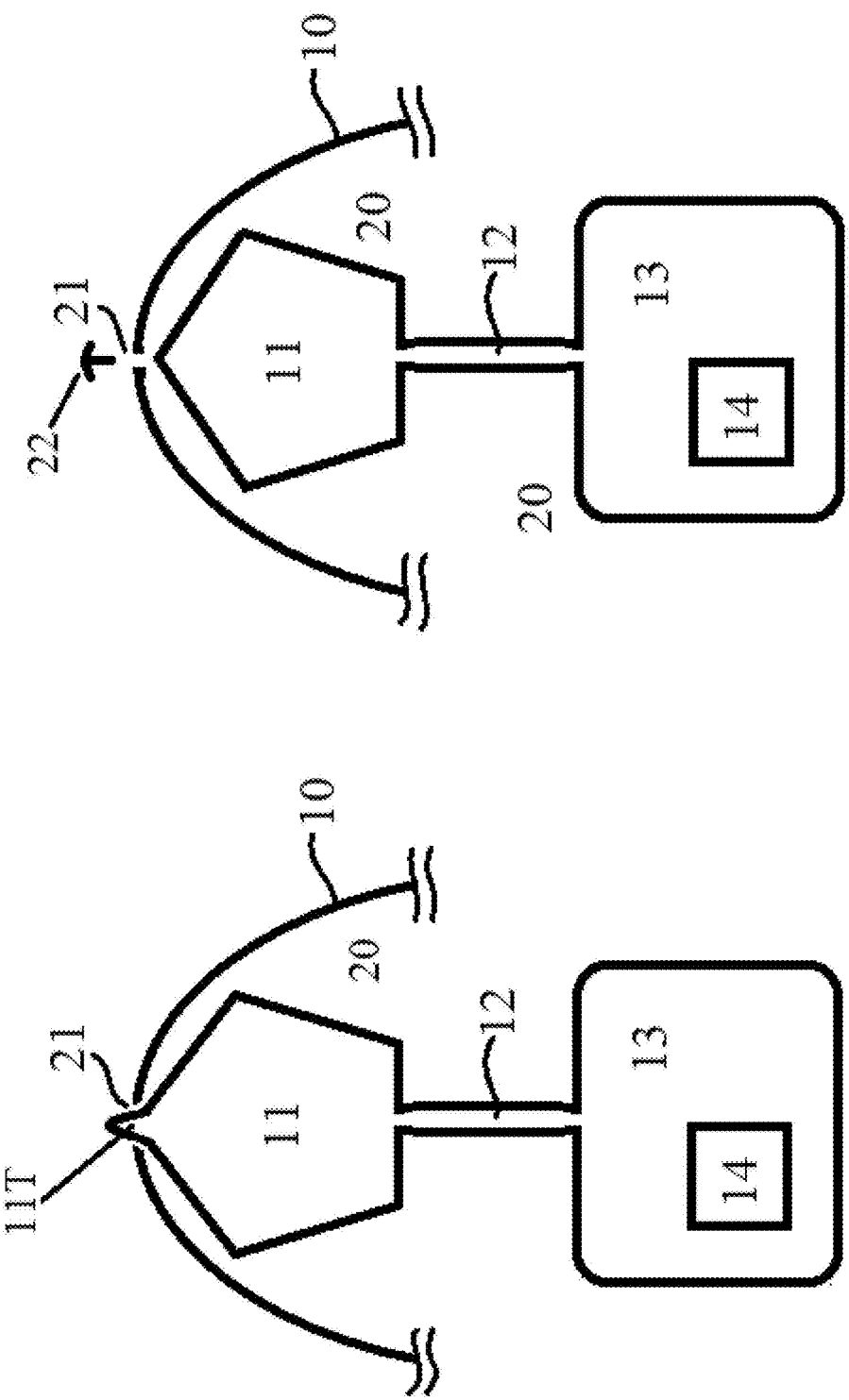
FIG. 1 is a sectional view that schematically shows sampling devices in accordance with an exemplary embodiment of the present invention.

Referring now to the sampling devices as shown in FIG. 1, the devices can entirely or partially enter into an intestinal tract, and can move along the intestinal tract for sampling a content contained therein. The term "content' as used in this embodiment may include human or animal gastrointestinal fluid, intestinal secretions, solid or semisolid, substances, slurry, feces, and stool etc. A housing 10 defines a chamber 20, which has a first opening (or inlet) 21. Housing 10 may be made of an inert material that does not cause irritation, such as polypropylene. In one embodiment, a sample collector 11 comprises a tongue 11T (or protrusion or outcrop 11T) that pokes out from the housing 10 through the first opening (or inlet) 21 to collect the content of the intestinal tract. In another embodiment, the sample collector 11 does not comprise such a tongue 11T poking out from the housing 10 through the first opening (or inlet) 21. Instead, the sample collector 11 in its entirety is located inside the chamber 20 and near the first opening 21 for collecting the sample content from the intestinal tract that has already passed through the first opening 21. In this design, an optional removable seal patch made of a material, such as cellulose acetate phthalate, glyceryl stearates, paraffin, or epoxy compounds, may removably cover the first opening 21. Alternatively, an optional plug 22 made of magnetic material coated with inert plastic may block or seal the first opening 21, and the magnetic plug seal 22 can be removed remotely with a magnetic field. If necessary, a vacuum system (not shown) may be employed to suck the intestinal content into the chamber through the first opening 21. The position of the sampling device can be monitored with ultrasound, X-ray, magnetic resonance imaging (MRI), or other means, and when the device reaches a predetermined position/section of the intestinal tract, the magnetic plug may be removed with a magnetic field by a physician, allowing the device to start collecting samples along the pathway in the intestinal tract.

Referring to FIG. 1 again, a collector driver 13 drives or runs the sample collector 11. A sample delivery 12 deliveries the sample collected by the sample collector 11 to the collector driver 13, using e.g. one or more convoy belts, as will be described in more details. The convoy belt used in the present invention is preferably motor-driven, thin, and sterile ribbon-belt. Samples from different sections of the intestinal tract can be collected into different locations of the convoy belt. Collector driver 13 may further include a sample depository 14 that stores the sample delivered by the sample delivery 12.

Figure 2A:
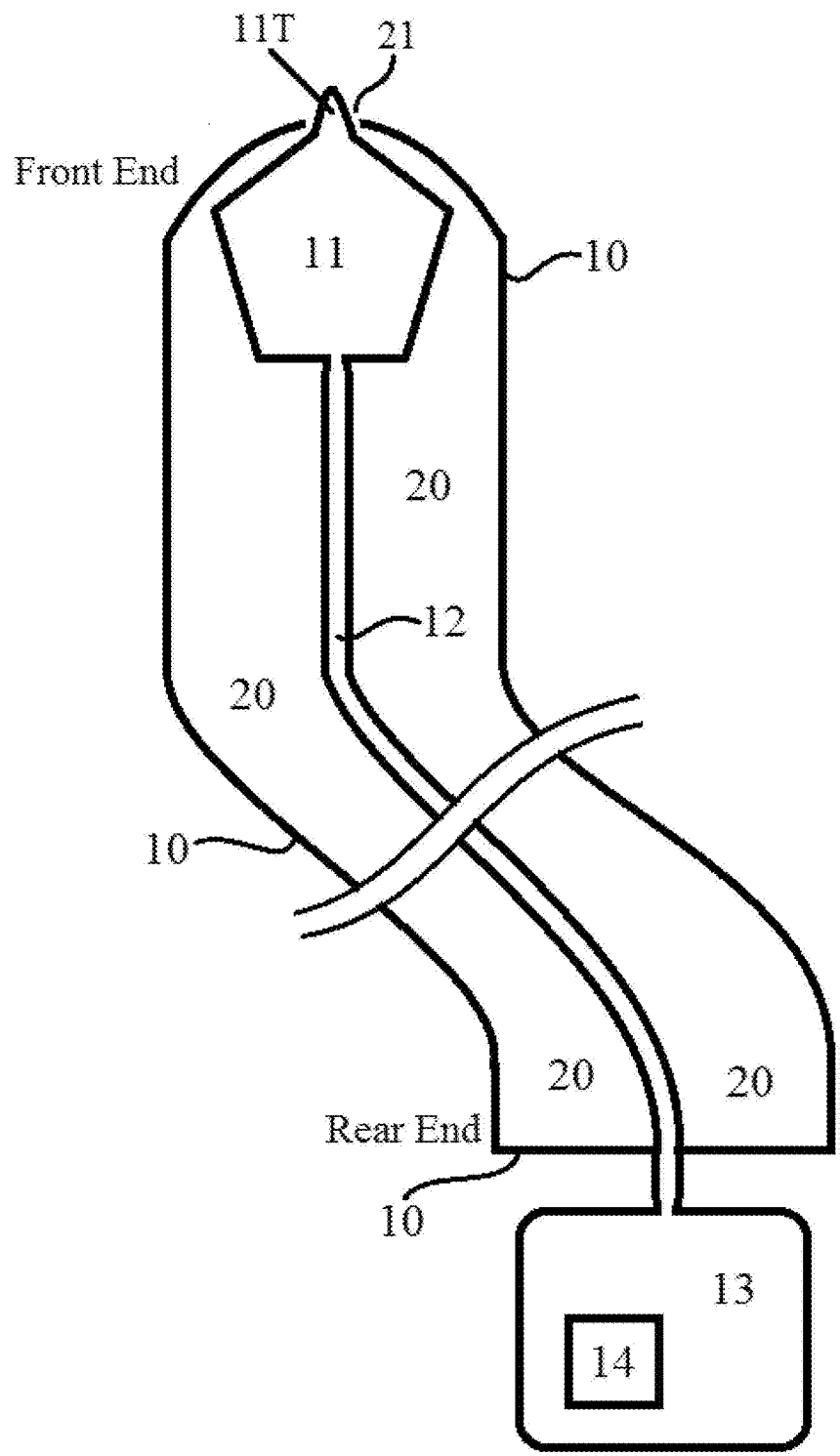
FIG. 2A is a sectional view that schematically demonstrates a probe-type sampling device with a tongue structure in accordance with an exemplary embodiment of the present invention.
Figure 2B:
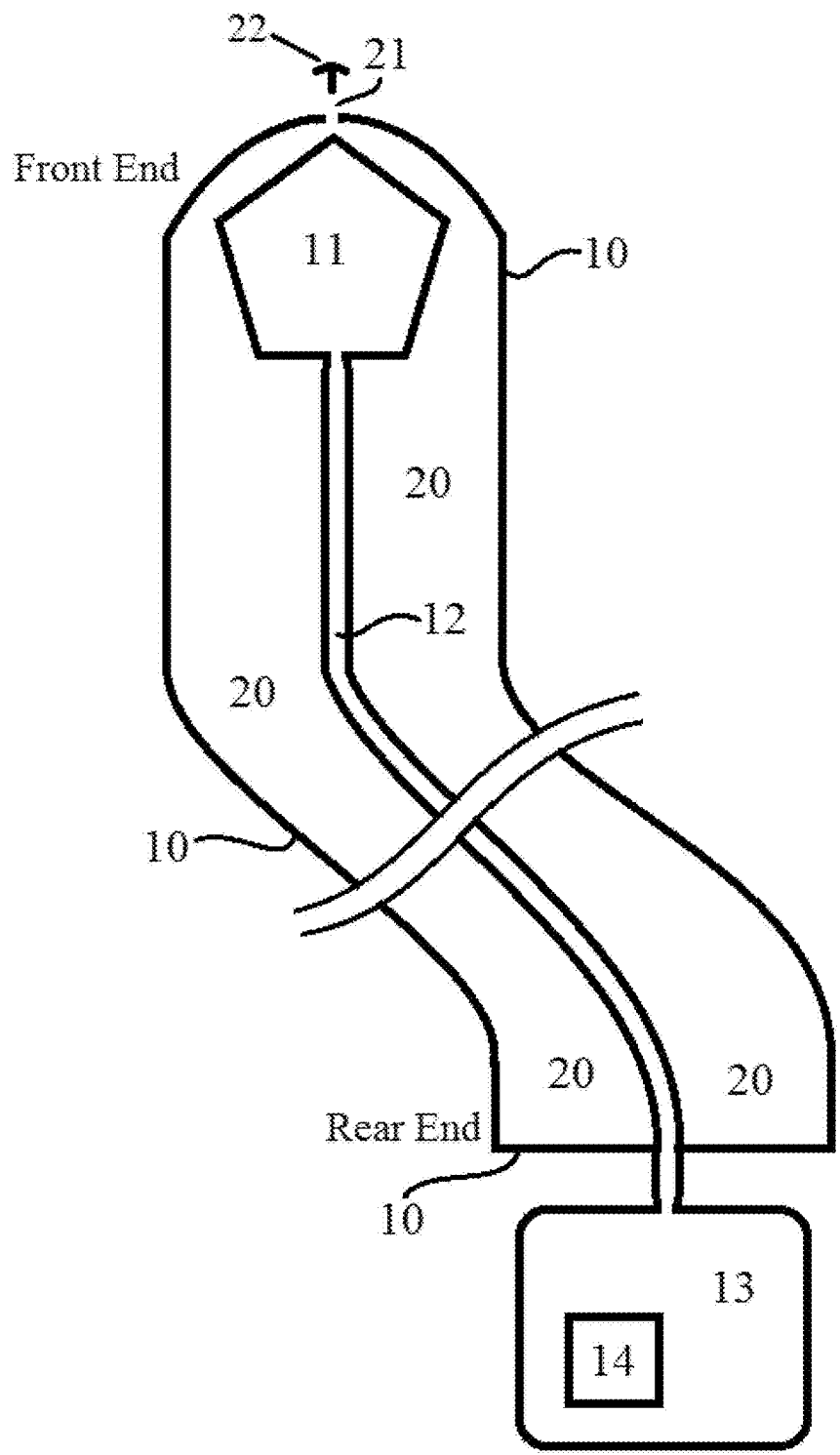
FIG. 2B is a sectional view that schematically demonstrates a probe-type sampling device without a tongue structure in accordance with an exemplary embodiment of the present invention.
Figure 3:
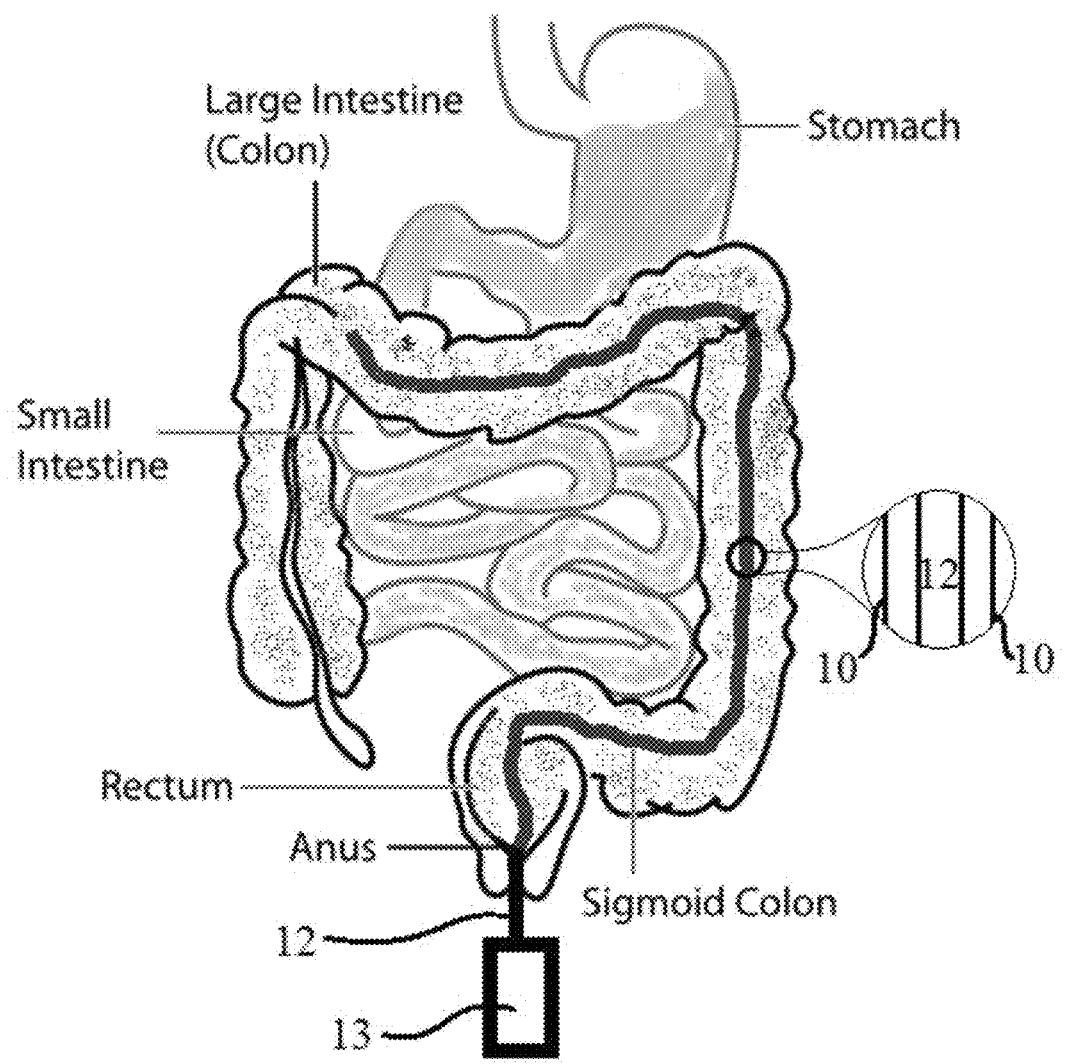
FIG. 3 is a sectional view that schematically illustrates the use of a probe-type sampling device in human gut in accordance with an exemplary embodiment of the present invention.

Referring to FIGS. 2A, 2B, and 3, the sampling device may be built like a probe, an endoscope, a gastric feeding tube, a duodenal feeding tube, or a gastrostomy. The housing 10 is a long and flexible tube that includes a front end with the first opening (or inlet) 21 for inserting into the intestinal tract through mouth or anus (as shown in FIG. 3), and a rear end located outside the intestinal tract. In an embodiment as shown in FIG. 2A, sample collector 11 comprises a tongue 11T that pokes out from the housing 10 through the first opening (or inlet) 21 to collect the content of the intestinal tract. In another embodiment as shown in FIG. 2B, sample collector 11 is entirely located inside the tube and near the front end, and does not have a tongue poking out from the housing 10. At least a part of the sample delivery 12 is located inside the tube, and the collector driver 13 may be completely located outside the tube near the rear end of the tube for a user to operate conveniently. Optionally, such sampling device design may include other components such as a light delivery system to illuminate the intestinal tract. The light source is normally outside the body and the light is typically directed via an optical fiber. A lens system may transmit the image from the objective lens to the viewer. One or more additional channels may be used to insert medical instruments or manipulators into the intestinal tract.

Figure 4A:
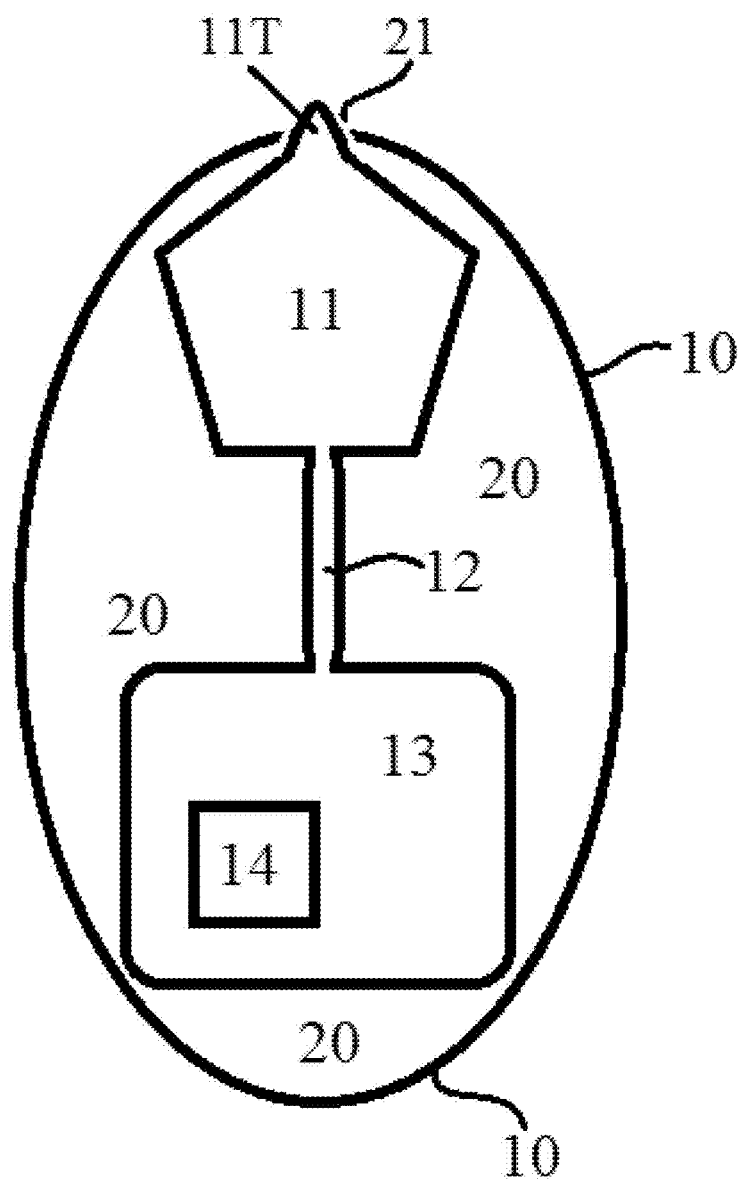
FIG. 4A is a sectional view that schematically shows a capsule-type sampling device with a tongue structure in accordance with an exemplary embodiment of the present invention.
Figure 4B:
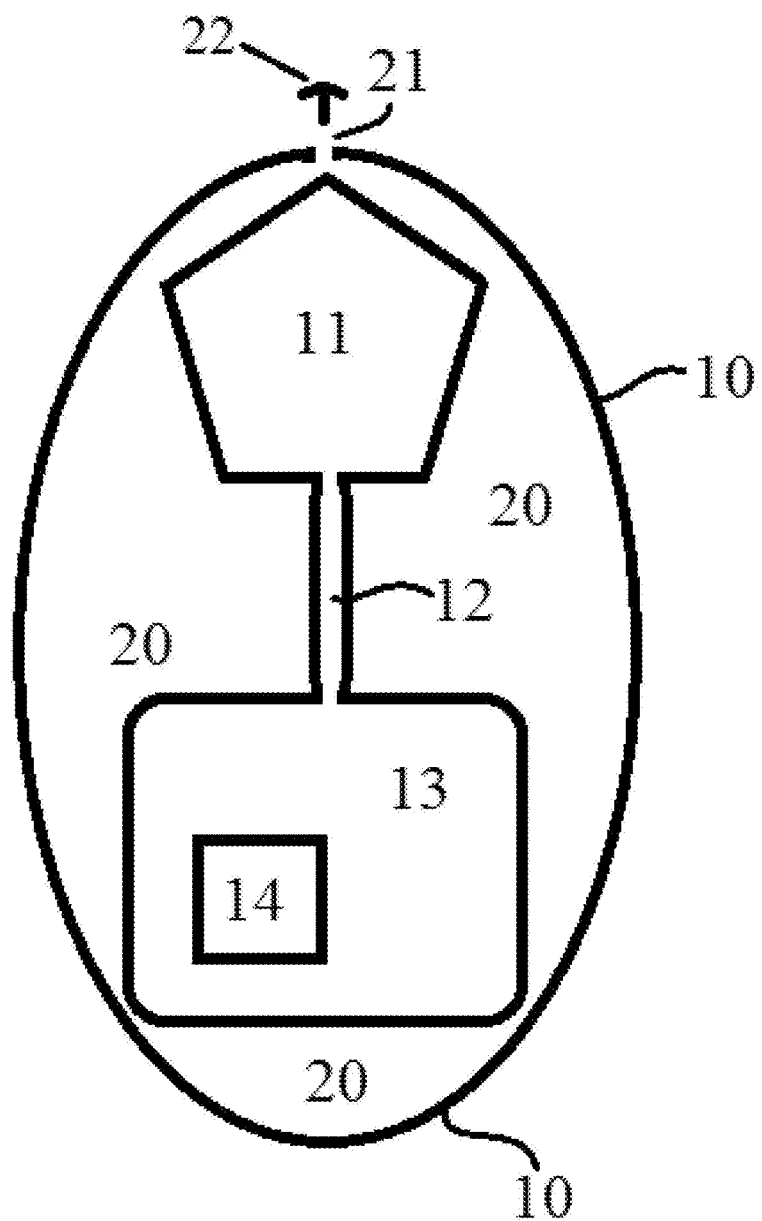
FIG. 4B is a sectional view that schematically shows a capsule-type sampling device without a tongue structure in accordance with an exemplary embodiment of the present invention.

Referring to FIGS. 4A and 4B, the sampling device may be built like tablet, capsule, or medicine pill for oral administration, or like a suppository for rectal administration. When the capsule is orally administered by a person or an animal, it can be recovered from the stool after the intestinal sampling is completed. The shape of the capsule may be elongated and may have rounded end portions and a circular or oval-shaped cross-section with, for example, a length of about 25 mm and a width of about 10 mm. In an embodiment as shown in FIG. 4A, sample collector 11 comprises a tongue 11T that pokes out from the housing 10 through the first opening (or inlet) 21 to collect the content of the intestinal tract. In another embodiment as shown in FIG. 4B, the entire sample collector 11, the sample delivery 12, and the collector driver 13 are all located inside the capsule chamber 20. Sample collector 11 does not include a tongue poking out from the housing 10.

Figure 5A:
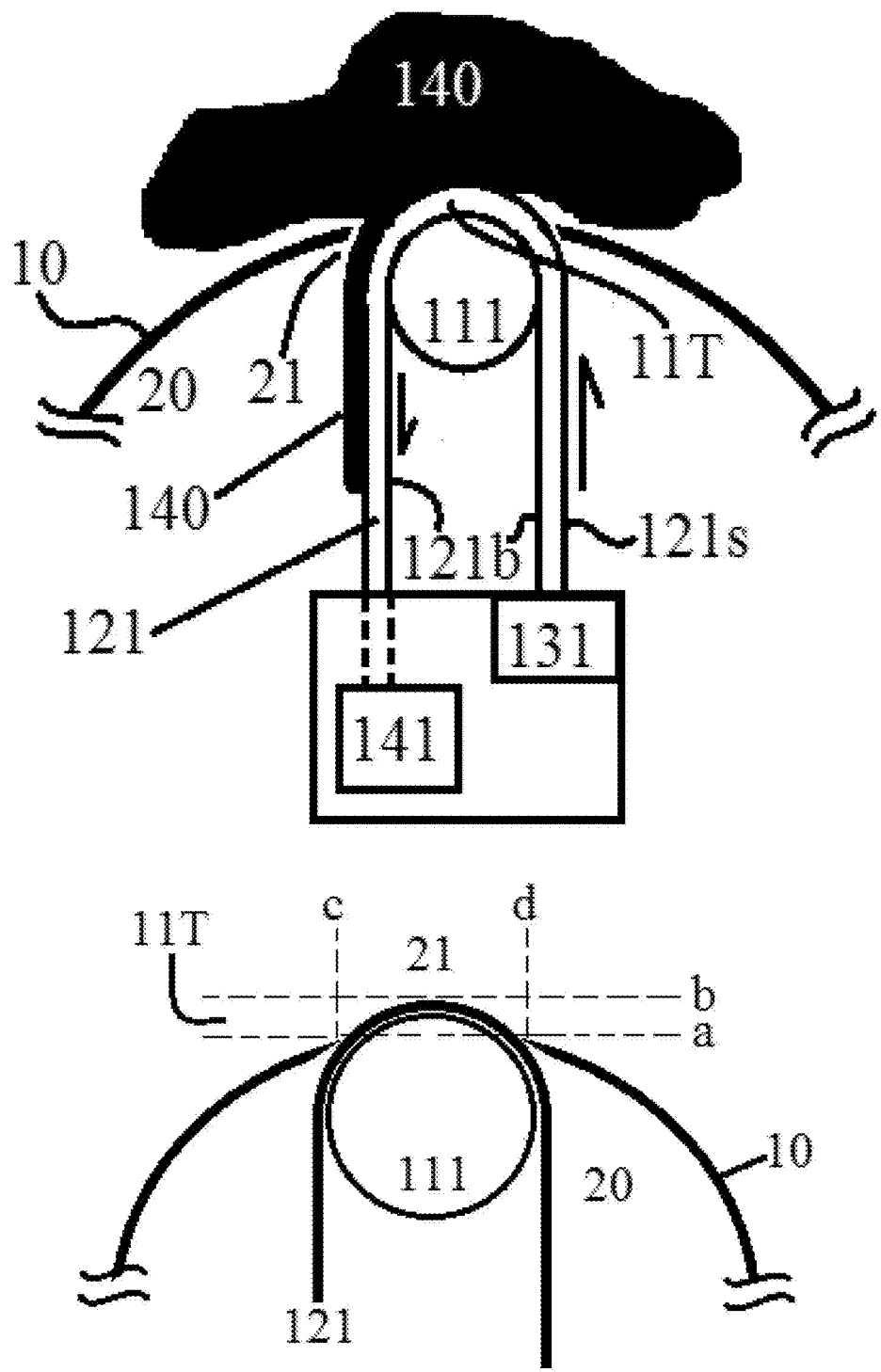
FIG. 5A is a sectional view that schematically depicts a sampling device using a single convoy belt and with a tongue structure in accordance with an exemplary embodiment of the present invention.
Figure 5B:
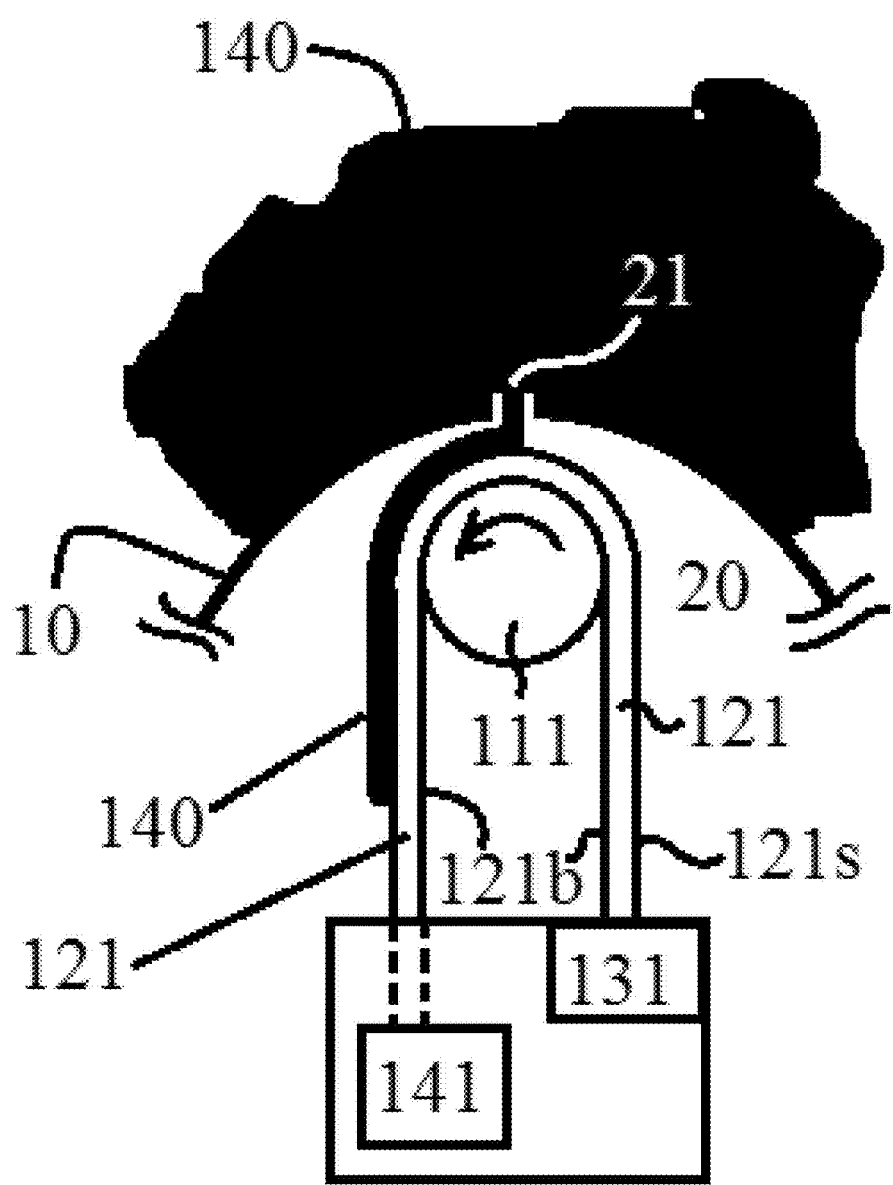
FIG. 5B is a sectional view that schematically depicts a sampling device using a single convoy belt and without a tongue structure in accordance with an exemplary embodiment of the present invention.

In various embodiments, sample collector 11 employs a rolling belt design to collect the intestinal content. FIGS. 5A and 5B show a single belt design. Sample collector 11 comprises a first cylindrical roller 111. The sample delivery 12 comprises a first convoy belt 121 having a first sampling surface 121s and a first back surface 121b. The collector driver 13 comprises a first belt source 131 for providing blank convoy belt 121. In an embodiment as shown in FIG. 5A, sample collector 11 comprises a tongue 11T that pokes out from the housing 10 through the first opening (or inlet) 21 to collect the content of the intestinal tract. Tongue 11T is defined as the portion of first convoy belt 121, or first convoy belt 121 and first cylindrical roller 111 in combination, that is located outside housing 10. In FIG. 5A, tongue 11T is the section of first cylindrical roller 111 and/or first convoy belt 121 around roller 111 within a space defined by conceptual house 10 boundary line a, conceptual belt 121 external boundary line b, as well as the boundary lines c and d of first opening (or inlet) 21. The length of tongue 11 is defined as the distance between parallel lines "a" and "b", and is preferably greater than 0, although the tongue length may be 0, or less than 0, in some embodiments. In operation, the first convoy belt 121 extends from the first belt source 131 and extends to the first cylindrical roller 111. Then belt 121 contacts the roller 111 with the first back surface 121b, and starts to wind around the roller 111. Shortly after that, belt 121 exits first opening 21 (i.e. passing line "a" upwardly), and then exposes its first sampling surface 121s to the content 140 in the intestinal tract. Sample content 140 is then loaded or absorbed on the first sampling surface 121s. Belt 121 reenters first opening 21 (i.e. passing line "a" downwardly), and then carries the loaded content 140 back through the sample delivery 12, and finally arrives at the sample depository 141. In the entire process, the collector driver 13 can apply a force to pull the first convoy belt 121 loaded with the sample 140 toward the sample depository 141.

In another embodiment as shown in FIG. 5B, first cylindrical roller 111 and first convoy belt 121 around roller 111 do not have a tongue 11T that pokes out from the housing 10 through the first opening (or inlet) 21. Instead, first cylindrical roller 111 and first convoy belt 121 in their entirety are located inside the chamber 20 and near the first opening 21 for collecting the sample content from the intestinal tract that has just passed through the first opening 21. In a sense, it is like that the tongue length has a negative value. In operation, the first convoy belt 121 similarly extends from the first belt source 131 and extends to the first cylindrical roller 111. Then belt 121 contacts the roller 111 with the first back surface 121b, and starts to wind around the roller 111. Shortly after that, belt 121 exposes its first sampling surface 121s to the content 140 from the intestinal tract that has just passed through the first opening 21. However, belt 121 does not exit and reenter first opening 21. Sample content 140 is then loaded or absorbed on the first sampling surface 121s Belt 121 carries the loaded content 140 back through the sample delivery 12 and finally arrives at the sample depository 141. In the entire process, the collector driver 13 can apply a force and pull, the first convoy belt 121 loaded with the sample 140 toward the sample depository 141.

Figure 6:
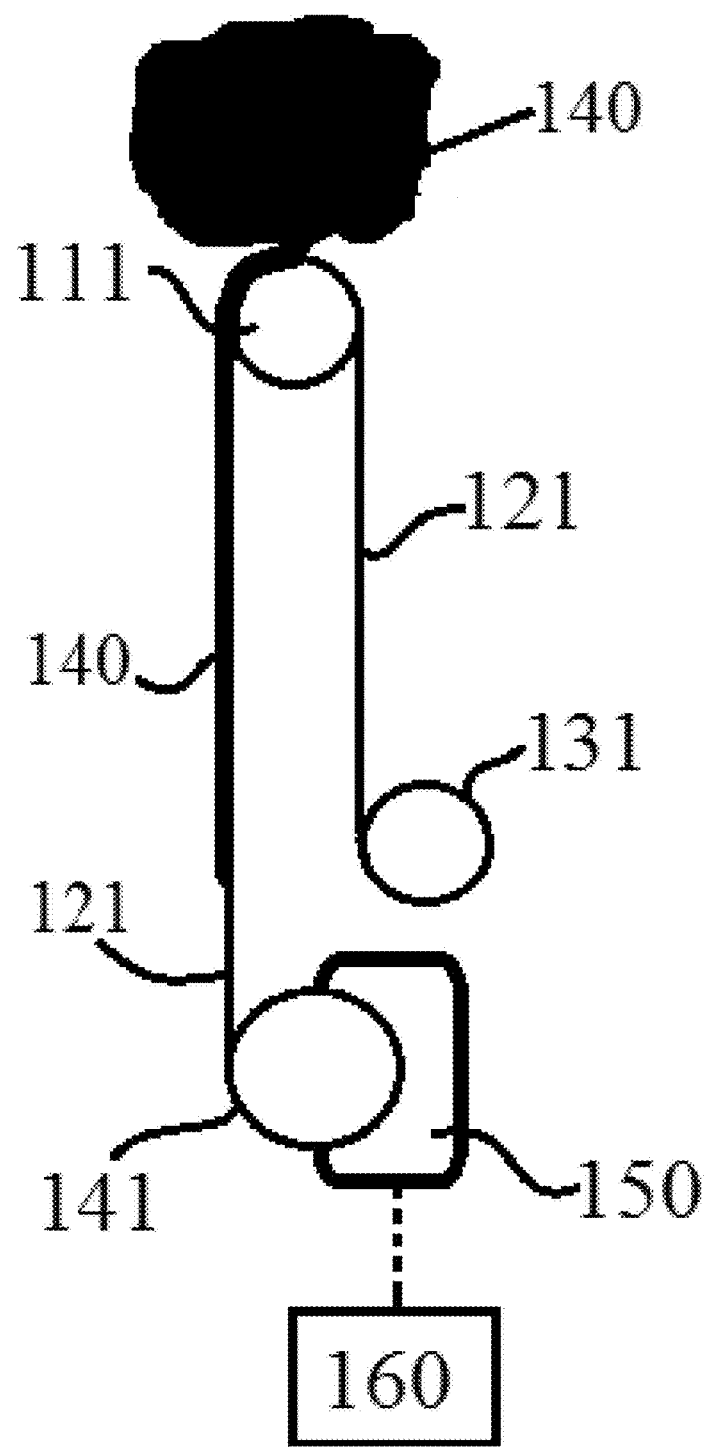
FIG. 6 is a sectional view that schematically illustrates a specific design of sampling device using a single convoy belt in accordance with an exemplary embodiment of the present invention.
Figure 12:
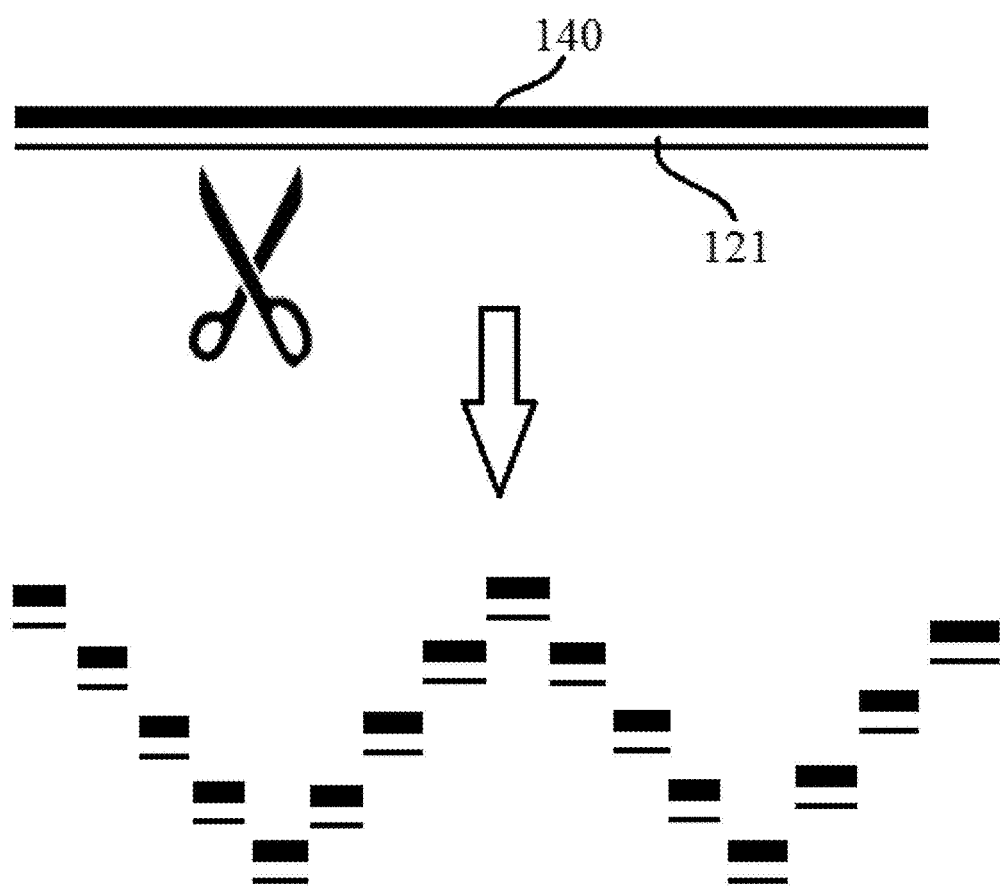
FIG. 12 shows that a single convoy belt loaded with intestinal sample is cut into many small pieces for detailed analysis in accordance with an exemplary embodiment of the present invention.
Figure 13:
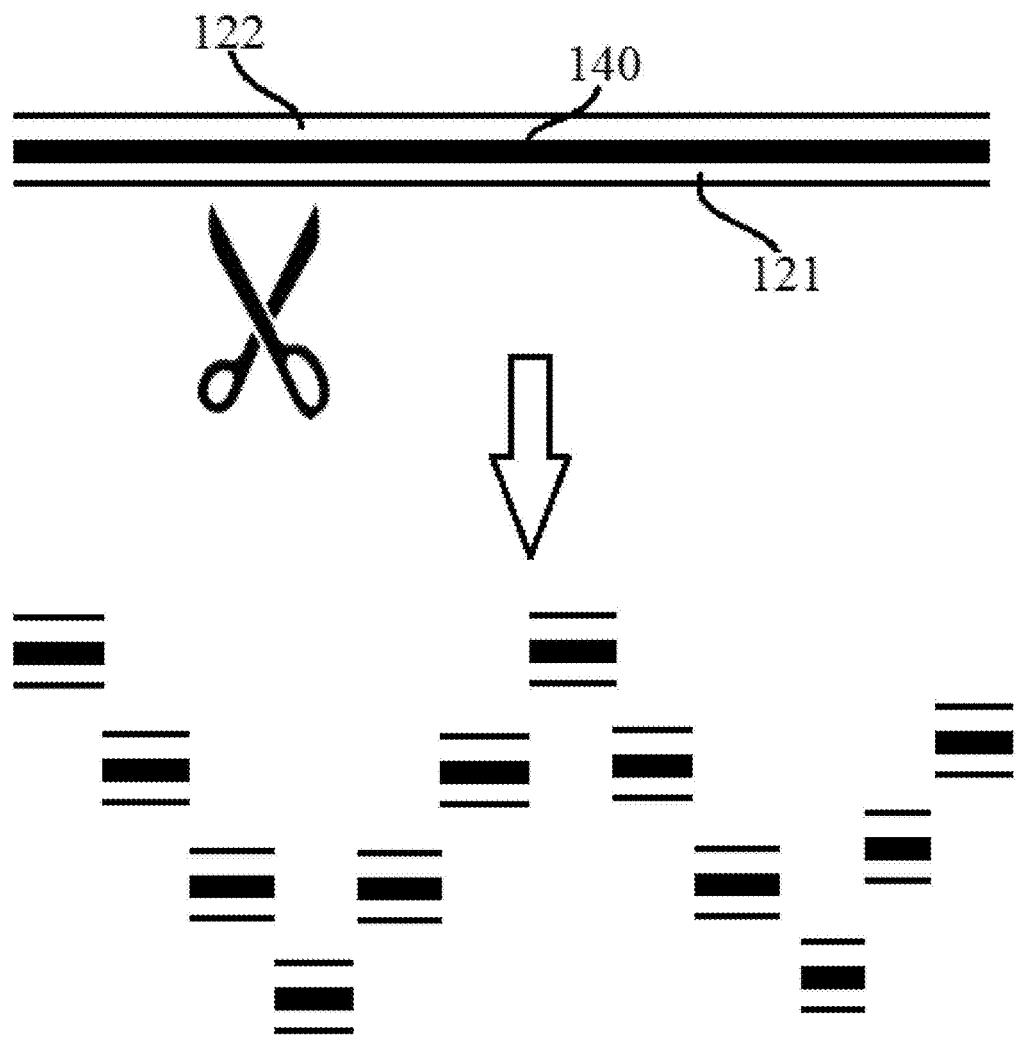
FIG. 13 shows that two convoy belts sandwiching intestinal sample is cut into many small pieces for detailed analysis in accordance with an exemplary embodiment of the present invention.

A specific embodiment of collector driver 13 that can be used in conjunction with the designs of FIGS. 5A and 5B is shown in FIG. 6. First belt source 131 comprises a roll/reel/spool of the first convoy belt 121 (fresh, blank and unloaded) around a roller. The sample depository may be a collection roll/reel/spool 141 around which the first convoy belt 121 already loaded with the sample 140 can coil or wrap, either clockwise or anticlockwise. The collector driver 13 may be further equipped with a motor 150 that can rotate the collection roll/reel/spool 141 and therefore pull the first convoy belt 121 loaded with the sample 140 toward the collection roll/reel/spool 141. In, a roll/reel/spool of belt 121 so obtained, first back surface 121b in one segment of the belt may contact the sampling surface 121s of a different segment of the belt. Therefore, first back surface 121b may be contaminated with "geographically mismatched" intestinal samples, and needs to be cleaned or decontaminated prior to the processing of the belt as shown in FIGS. 12 and 13.

The sampling device of the invention may further include a controller 160 to manage the operation of the device. An external power source (not shown) may be configured to power the motor 150. Alternatively, an internal power source such as a voltaic cell using the body fluid as the electrolyte/salt bridge, a wafer battery, or an inductively rechargeable battery may be configured to power the motor 150, particularly for capsule-type devices. Inductive charging (also known as wireless charging) uses an electromagnetic field to transfer energy between two a charging device and a battery through electromagnetic induction. Induction charging devices use an induction coil to create an alternating electromagnetic field, and a second induction coil in the sampling device takes power from the electromagnetic field and converts it back into electric current to charge the battery. The two induction coils in proximity combine to form an electrical transformer. Greater distances between sender and receiver coils can be achieved when the inductive charging system uses resonant inductive coupling.

Figure 7A:
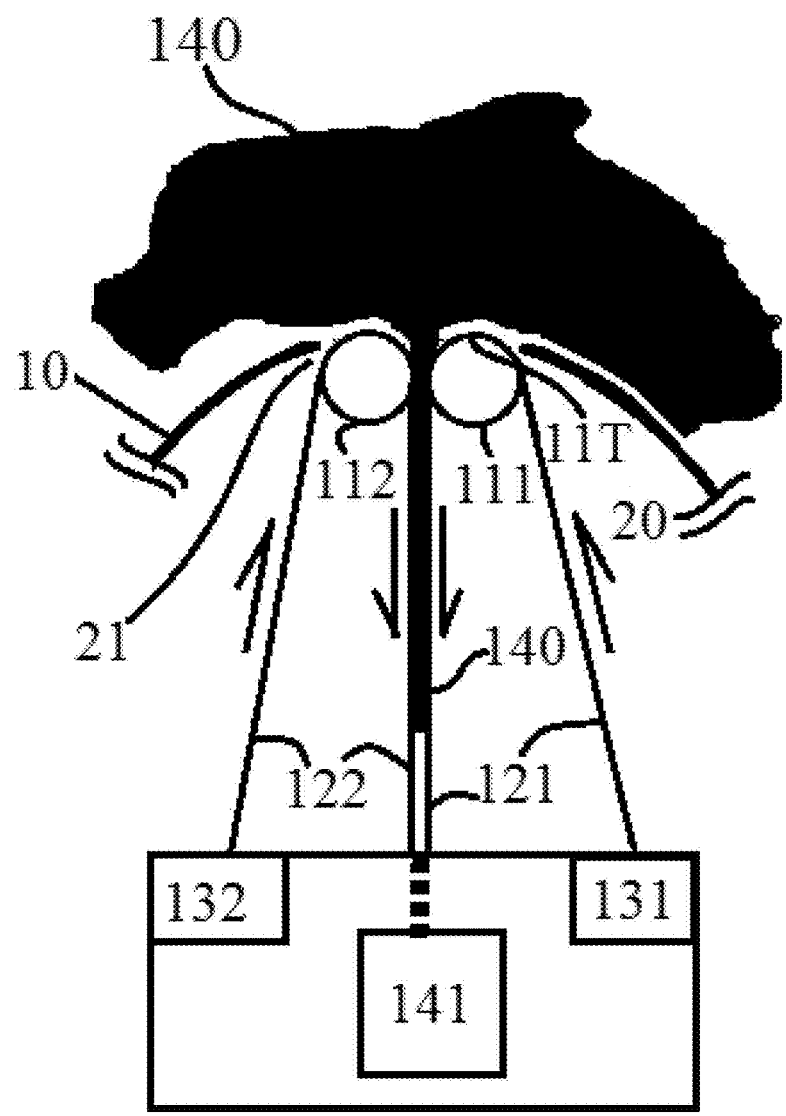
FIG. 7A is a sectional view that schematically depicts a sampling device using two convoy belts and with a tongue structure in accordance with an exemplary embodiment of the present invention.
Figure 7B:
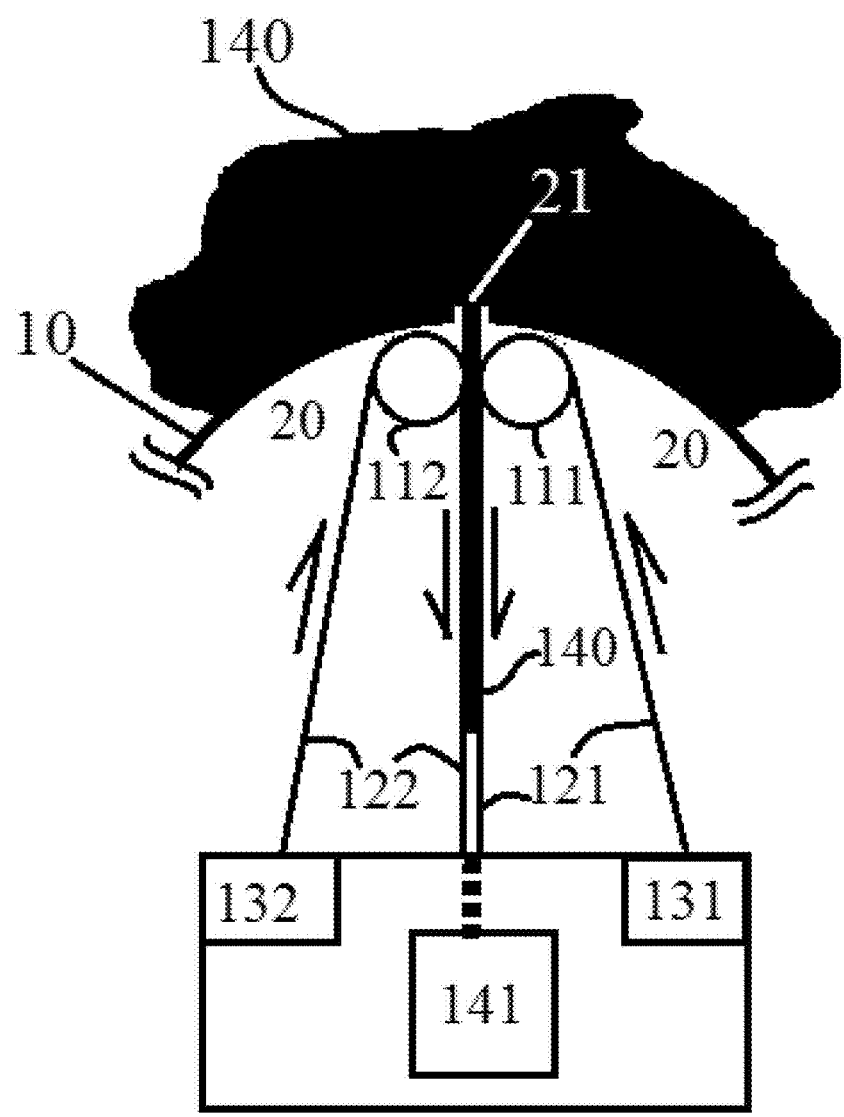
FIG. 7B is a sectional view that schematically depicts a sampling device using two convoy belts and without a tongue structure in accordance with an exemplary embodiment of the present invention.
Figure 7B:

Referring to a double belt design as shown in FIGS. 7A and 7B that is based on the single belt design as shown in FIGS. 5A and 5B, the sample collector 11 further comprises a second cylindrical roller 112. The sample delivery 12 further comprises a second convoy belt 122 having a second sampling surface 122s and a second back surface 122b. The collector driver 13 further comprises a second belt source 132 for providing the second convoy belt 122 which is blank. The axes of two cylindrical rollers 111 and 112 are in parallel with each other, and their centers are substantially equally distant from the first opening 21. Rollers 111 and 112 have a gap between them. Rollers 111 and 112 work together like twin roller strip caster, in which the two rollers have parallel axes and are spaced apart from each other by a distance corresponding to the desired thickness of the cast strip. Content 140, like ingot steel, is fed or supplied to the gap between two oppositely-rotating casting rolls 111 and 112, forming a sheet-like sample that can be rolled in sample depository 141.

In an embodiment as shown in FIG. 7A, sample collector 11 comprises a tongue 11T that pokes out from the housing 10 through the first opening (or inlet) 21 to collect the content of the intestinal tract. Similar to FIG. 5A embodiment, tongue 11T is also defined as the portion of belts 121 & 122, or belts 121 & 122 in combination with rollers 111 & 112, that is located outside (or not within) housing 10. Similarly to the operation of FIG. 5A embodiment, first convoy belt 121 exits and reenters first opening 21. Belt 121 passes through the gap after it is loaded with the content 140 on the first sampling surface 121s, and then carries the loaded content 140 through the sample delivery 12 to the sample depository 141. Belt 122 operates in a symmetrical manner with belt 121. Second convoy belt 122 also exits and reenters first opening 21. Belt 122 extends from the second belt source 132 to the second cylindrical roller 112, and contacts the roller 112 with its second back surface 122b. Then belt 122 winds around the second cylindrical roller 112. In doing so, belt 122 will expose its second sampling surface 122s to the content 140 right in the intestinal tract, and will load the content 140 on sampling surface 122s Therefore, the contents 140 on surfaces 121s and 122s will meet each other and be squeezed together when belts 121 & 122 pass the gap between two rollers 111 & 112. The gap is configured to be narrower than the thickness of combined belts 121 & 122 with content 140, so that content 140 is completely squeezed between the two surfaces 121s and 122s, and completely loaded on, or sandwiched/encapsulated between, both surfaces. Belts 121 & 122 both pass through the gap between rollers 111 and 112, and carry the loaded content 140 through the sample delivery 12 to the sample depository 141. Such a "sandwich" or "encapsulation" configuration helps to preserve the sample 140's in-vivo environmental integrity, and to prevent cross contamination between different samples on the same belt. At last, the collector driver 13 pulls the two convoy belts 121 & 122 loaded with the combined contents 140 at a same speed toward the sample depository 141.

In an embodiment as shown in FIG. 7B, sample collector 11 does not have a tongue 11T that pokes out from the housing 10 through the first opening (or inlet) 21. Similarly to the operation of FIG. 5B embodiment, first convoy belt 121 passes through the gap after it is loaded with the content 140 on the first sampling surface 121s, and then carries the loaded content 140 through the sample delivery 12 to the sample depository 141. Belt 122 operates in a symmetrical manner with belt 121. Second convoy belt 122 extends from the second belt source 132 to the second cylindrical roller 112, and contacts the roller 112 with its second back surface 122b. Then belt 122 winds around the second cylindrical roller 112. In doing so, belt 122 will expose its second sampling surface 122s to the content 140 from the intestinal tract that has just passed through the first opening 21 of the housing 10, and will load the content 140 on sampling surface 122s. In other words, belts 121 & 122 work together to receive content 140 that has just passed through the first opening 21. Therefore, the content 140 falls into the gap between surfaces 121s and 122s. The gap is configured to be so narrow that content 140 is completely squeezed between the two surfaces 121s and 122s, and completely loaded on, or sandwiched/encapsulated between, both surfaces. Belts 121 & 122 both pass through the gap between rollers 111 and 112, and carry the loaded content 140 through the sample delivery 12 to the sample depository 141. Such a "sandwich" or "encapsulation" configuration helps to preserve the sample 140's in-vivo environmental integrity, and to prevent cross contamination between different samples on the belt. At last, the collector driver 13 pulls the two convoy belts 121 & 122 loaded with the combined contents 140 at a same speed toward the sample depository 141.

Figure 8:
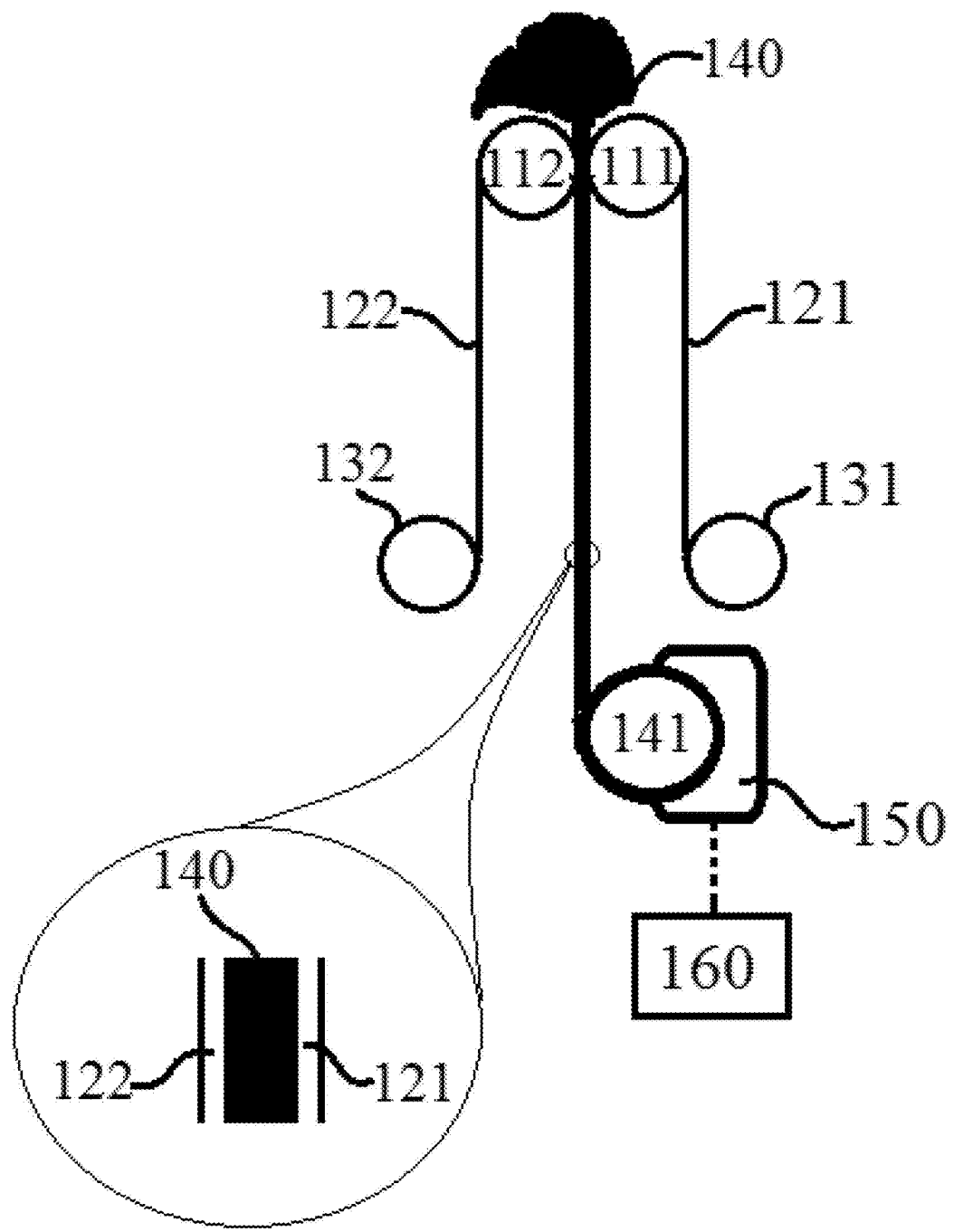
FIG. 8 is a sectional view that schematically illustrates a specific design of sampling device using two convoy belts in accordance with an exemplary embodiment of the present invention.

For collector driver 13, a specific embodiment is shown in FIG. 8. Similar to FIG. 6, first belt source 131 comprises a roll/reel/spool of the first convoy belt 121 (fresh, blank and unloaded) around a roller. Second belt source 132 comprises a roll/reel/spool of the second convoy belt 122 (fresh, blank and unloaded) around another roller. The sample depository comprises a collection roll/reel/spool 141 around which the combined contents 140 sandwiched between the two convoy belts 121 & 122 can coil or wrap. Similarly, the collector driver 13 may be further equipped with a motor 150 that can rotate the collection roll/reel/spool 141 and therefore pull the combined contents 140 sandwiched between the two convoy belts 121 & 122 toward the collection roll/reel/spool 141. The sampling device in this embodiment may further include a controller 160 to manage the operation of the device. An external power source (not shown) may be configured to power the motor 150. Alternatively, an internal power source such as a wafer battery or an inductively rechargeable battery may be configured to power the motor 150, especially for capsule-type devices. As an advantage of this embodiment, in a roll/reel/spool of belts 121/122 so obtained, first back surface 121b/122b in one segment of the belt 121/122 do not contact the sampling surface 121s/122s of a different segment of the belt. Therefore, first back surface 121b/122b is not contaminated with "geographically mismatched" intestinal samples, and does not need to be cleaned or decontaminated prior to the processing of the belt as shown in FIGS. 12 and 13.

Figure 9A:
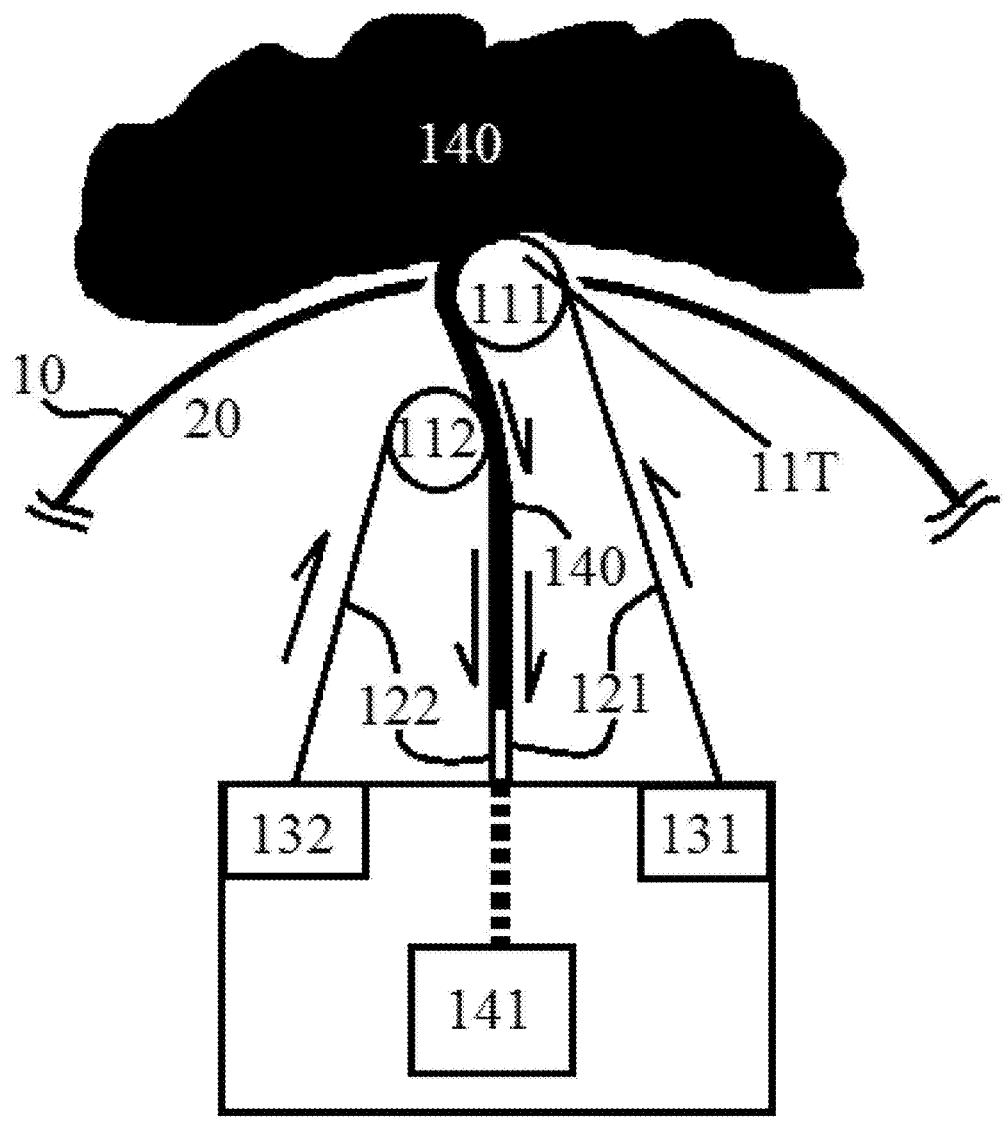
FIG. 9A is a sectional view that schematically depicts another sampling device using two convoy belts and with a tongue structure in accordance with an exemplary embodiment of the present invention.
Figure 9A:
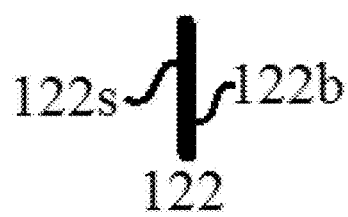
Figure 9A:
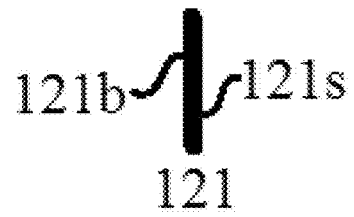
Figure 9B:
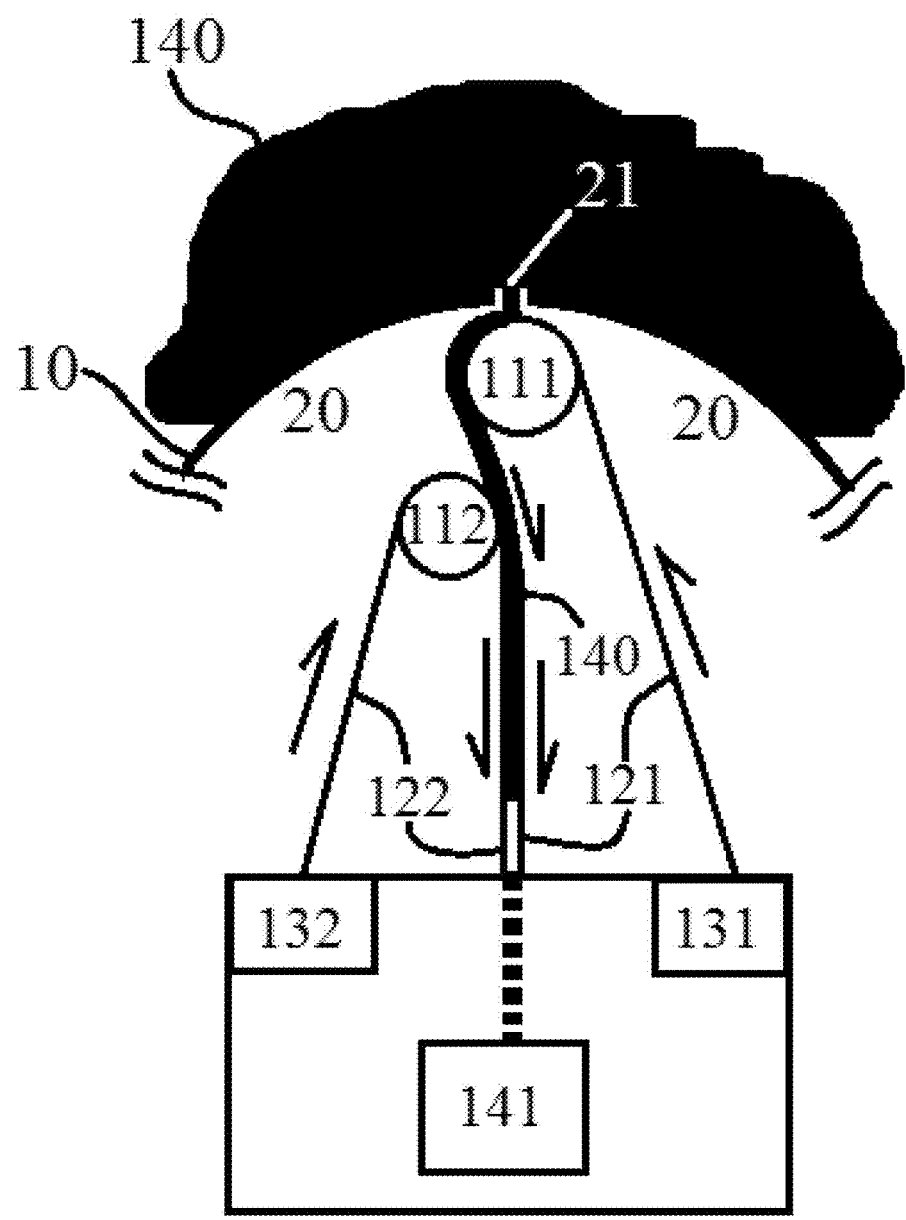
FIG. 9B is a sectional view that schematically depicts another sampling device using two convoy belts and without a tongue structure in accordance with an exemplary embodiment of the present invention.
Figure 9B:
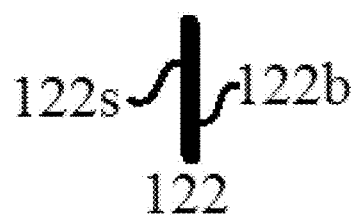
Figure 9B:
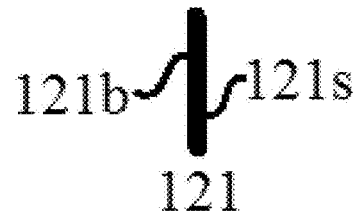

Referring to another double belt design as shown in FIGS. 9A and 9B that is based on the embodiments of FIGS. 7A and 7B as described above, the sample collector 11 further comprises a second cylindrical roller 112. Similar to FIG. 5A, sample collector 11 in FIG. 9A includes a tongue 11T. Similar to FIG. 5B, sample collector 11 in FIG. 9B does not have such a tongue 11T. The sample delivery 12 further comprises a second convoy belt 122 having a second sampling surface 122s and a second back surface 122b. The collector driver 13 further comprises a second belt source 132 for providing the second convoy belt 122 which is blank. The two cylindrical rollers 111 and 112 are in parallel with each other; however, the first cylindrical roller 111 is closer to the first opening 21 than the second cylindrical roller 112. Belt 122 operates in an asymmetrical manner with belt 121. As a result, after the second convoy belt 122 extends to, contact, and wind around the second cylindrical roller 112, belt 122 exposes its second sampling surface 122s only to the content 140 that has already been loaded on the first sampling surface 121s. Belt 122 does not directly expose to the content 140 that is right in the intestinal tract (as shown in FIG. 9A) or that has just passed through the first opening 21 (as shown in FIG. 9B), because roller 111 and belt 121 block the exposure of belt 122 to content 140. Belt 122 then encapsulates or sandwiches the content 140 on the first sampling surface 121s with its surfaces 122s, and moves along the first convoy belt 121 through the sample delivery 12 to the sample depository 141. Collector driver 13 is configured to pull the two convoy belts 121 & 122 at a same speed toward the sample depository 141.

Figure 10:
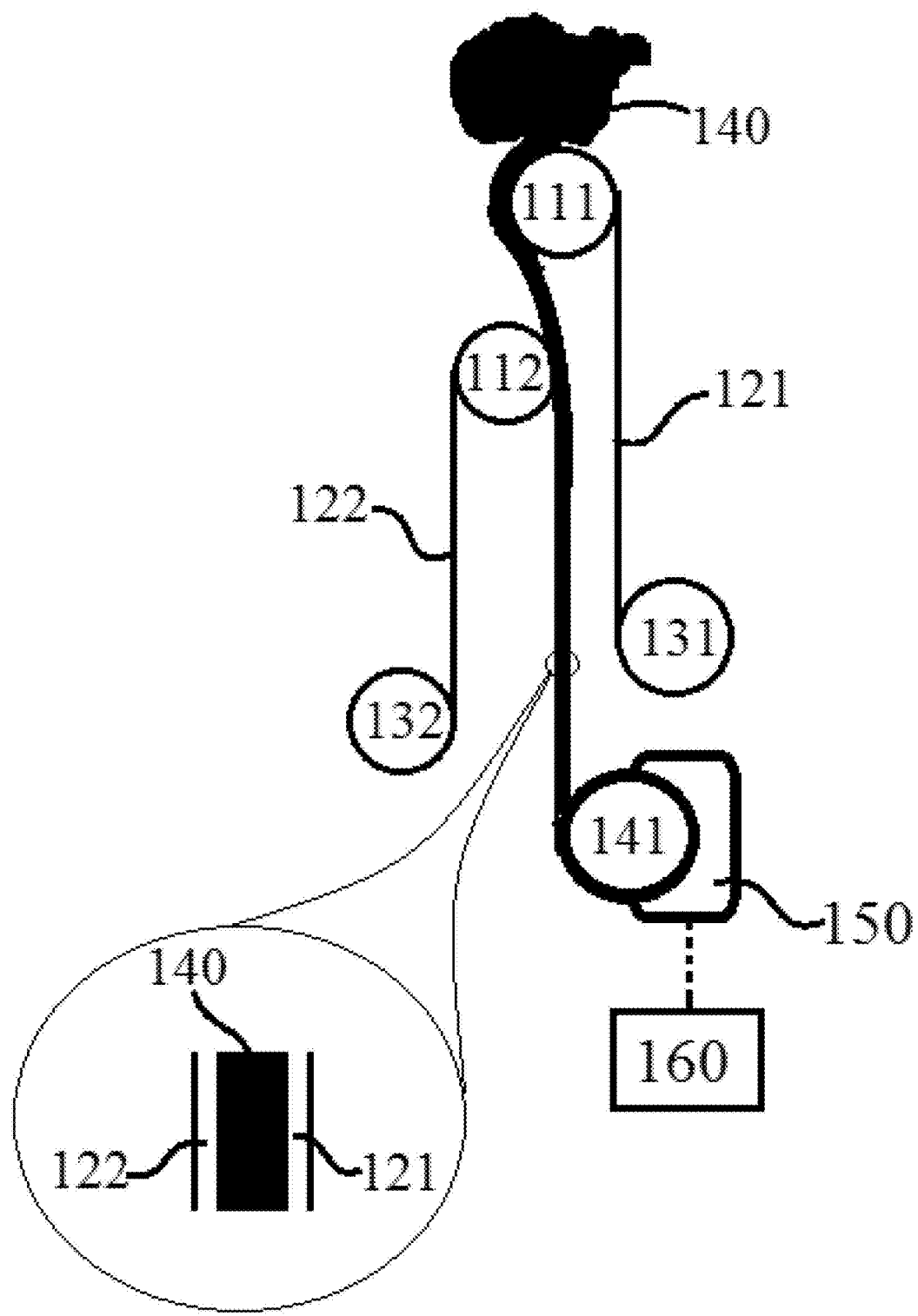
FIG. 10 is a sectional view that schematically illustrates another specific design of sampling, device using two convoy belts in accordance with an exemplary embodiment of the present invention.

For collector driver 13, a specific embodiment is shown in FIG. 10, which is similar to FIGS. 8 and 6, and the details thereof will not be repeated here for conciseness. Similarly, in a roll/reel/spool of belts 121/122 so obtained, first back surface 121b/122b in one segment of the belt 121/122 do not contact the sampling surface 121s/122s of a different segment of the belt. Therefore, first back surface 121b/122b is not contaminated with "geographically mismatched" intestinal samples, and does not need to be cleaned or decontaminated prior to the processing of the belts as shown in FIGS. 12 and 13.

Figure 11:
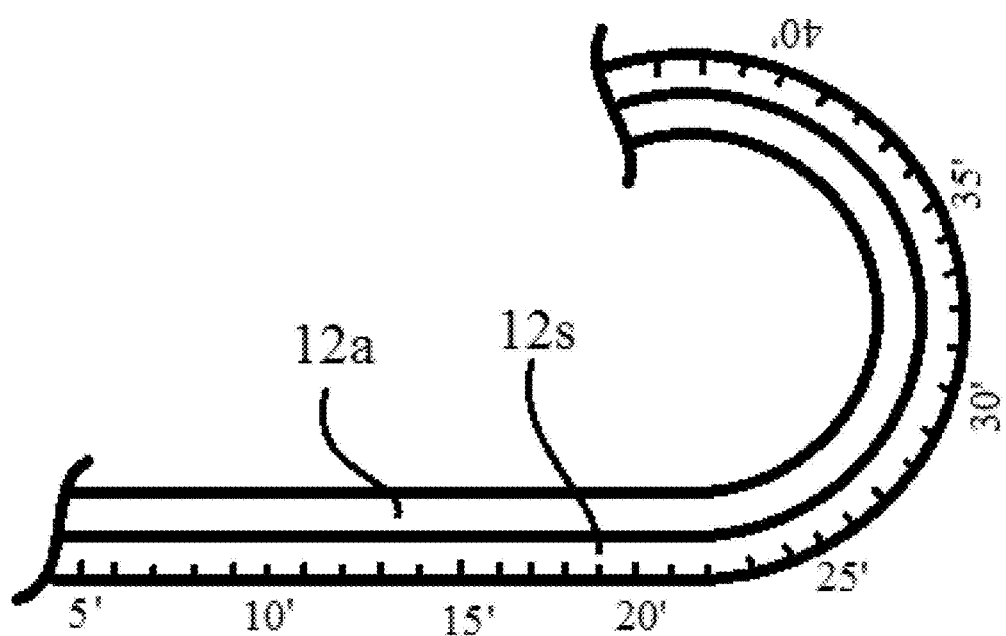
FIG. 11 schematically illustrates the structure of a convoy belt in accordance with an exemplary embodiment of the present invention.

In various embodiments, the convoy belt of the invention may include two layers joined together, a substrate layer having a back surface as described above, and an adsorbent layer having a sampling surface as described above. As shown in FIG. 11, substrate layer 12s may be a strip of fabric made of multiple plies of a material such as polyester (PES), Nylon or polyamide (PA). The substrate layer 12s functions to increase the tensile strength of the convoy belt 121/122 used in the present invention, and to survive the force that pulls them toward the sample depository 141. The adsorbent layer 12a is preferably continuous, homogenous, flat, smooth and free of any indentations and pockets, and may comprise a material selected form sodium carboxymethylcellulose, polyacrylamide, polyacrylonitrile and acrylic acid polymers, cross-linked acrylic, Karaya gum and polysaccharides. Adsorbent layer 12a may be cured from a monomer solution applied to or impregnated within the substrate layer 12s.

In a preferred embodiment, convoy belts 121 and/or 122 as described above may be marked with length indicators. The sampling device may be configured to, or programmed to, correlate (A) the specific intestinal sample 140 loaded on the belt 121/122 at a length indicator (e.g. 35 inches) to (B) the location in the intestinal tract where that sample is collected (e.g. 6 feet away from the mouth). With the correlation, a user can establish (1) the spectrum of biochemical products as a function of the intestinal tract length; (2) the spectrum of biochemical reactions as a function of the intestinal tract length; (3) the spectrum of microbes as a function of the intestinal tract length; (4) the spectrum of byproducts of all microbes as a function of the intestinal tract length; and (5) the spectrum of aerobic/anaerobic distribution and associated conditions as a function of the intestinal tract length.

In an embodiment, convoy belt 122 as described above may be a simple covering belt with no adsorbent layer 12a, and such a covering belt may simply be used to seal, cover, or encapsulate belt 121 that is loaded with intestinal sample 140.

In some embodiments, belt 121 may function as a sample wipe or a sample trap. It may be made of paper, cotton cloth or porous PTFE (Teflon), for example, an open weave fiberglass fabric coated with a layer of PTFE.

The present invention also provides a process of sampling content in an intestinal tract using the sampling device as describe above. The process includes:

(1) inserting the sampling device entirely or partially into the intestinal tract;

(2) moving the sampling device along the intestinal tract;

(3) collecting the content in the intestinal tract in the sample collector 11; and (4) delivering the sample content collected by the sample collector to the collector driver 13.

In an embodiment, the process further comprises providing a convoy belt, and continuously loading the sample content collected from the intestinal tract.

The sample depository 141 with the collected sample is subsequently sent or handed over to a medical institution or laboratory, where the sample is analyzed. The loaded belt 121 or belts 121/122 may mirror the content of at least a segment of the intestinal tract along its length, and can be cut into pieces to establish the spectrum of intestinal content in that segment. With a sufficient number of measurements, a user can conduct sample chemical analysis, microbe strains/colonies identification and characterization along the entire intestinal tract. Referring to FIG. 12, the first convoy belt 121 loaded with the sample 140 may be cut into pieces for analyzing the sample content 140, as a function of intestinal tract length. Referring to FIG. 13, two convoy belts 121 & 122 loaded with the combined contents 140 are cut into pieces for analyzing the sample content 140, as a function of intestinal tract length.

These pieces in FIGS. 11 and 12 are useful for establishing the following medical information associated with healthy or unhealthy individuals: (1) the spectrum of biochemical products as a function of the intestinal tract length, e g as a result of any specific diet; (2) the spectrum of biochemical reactions as a function of the intestinal tract length; (3) the spectrum of microbes as a function of the intestinal tract length, (4) the spectrum of byproducts of all microbes as a function of the intestinal tract length, (5) the spectrum of aerobic/anaerobic distribution and associated conditions as a function of the intestinal tract length; (6) the interaction of a) the normal biochemical reactions, b) the microbes, and c) the microbe byproducts that causes several major diseases, as a function of the intestinal tract length; (7) data necessary to identify and characterize physiological, biochemical or other bio-engineering processes; (8) the microbial flora distribution for the intestinal tract as a function of the intestinal tract length; and (9) the ratios of solids, liquids, and gases, as well as, their compositions, temperature, partial pressures, and other variables, as a function of the intestinal tract length.

Figure 14:
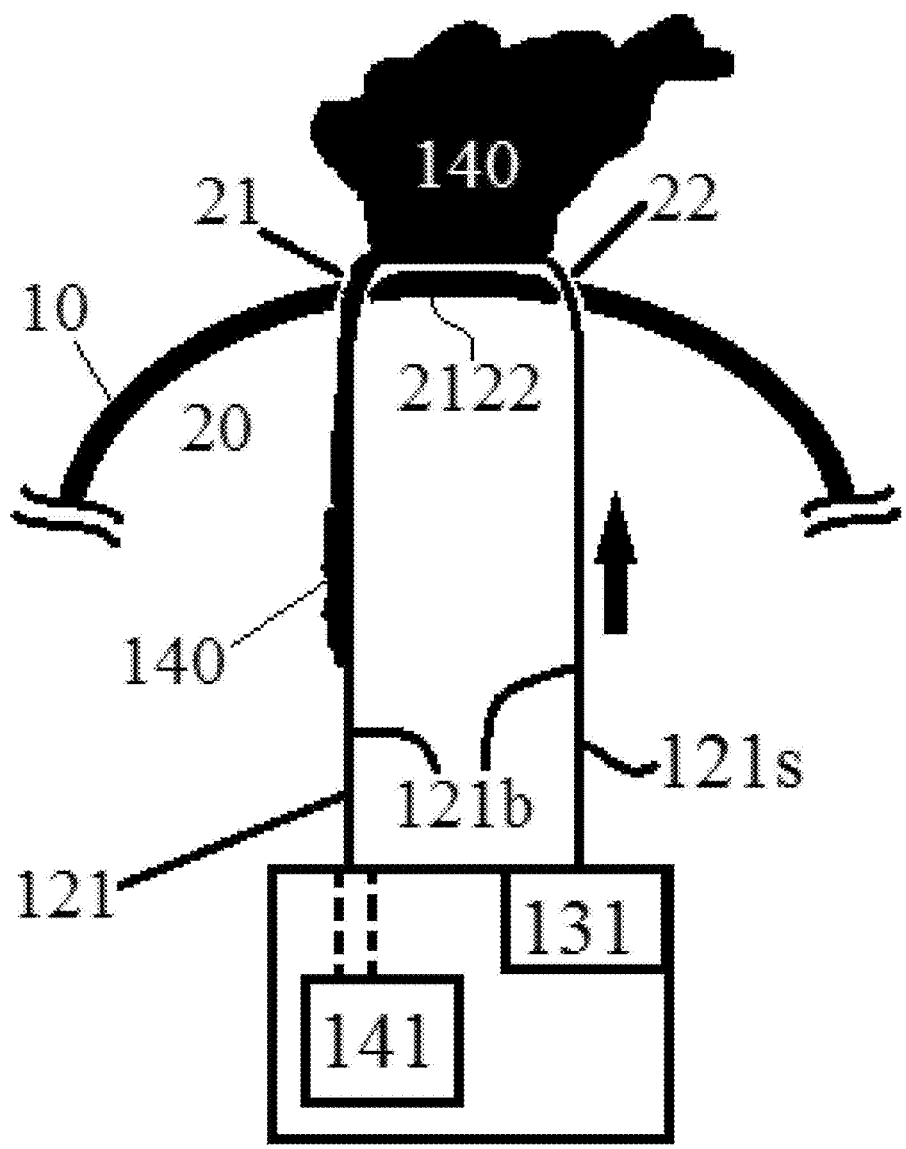
FIG. 14 is a sectional view that schematically depicts a sampling device using two openings on the chamber in accordance with an exemplary embodiment of the present invention.

The embodiments as shown in FIGS. 5A, 5B and 6 can be modified in any suitable manner. In a modified embodiment as shown in FIG. 14, the chamber 20 further comprises a second opening 22. Therefore, sample collector 11 comprises a first bridge 2122 formed between the first opening 21 and the second opening 22. First cylindrical roller 111 may be removed from the embodiment. Similarly, the sample delivery 12 comprises a first convoy belt 121 having a first sampling surface 121s and a first back surface 121b. The collector driver 13 comprises a first belt source 131 for providing the first convoy belt 121 which is blank. In this embodiment, the first convoy belt 121 is configured to extend from the first belt source 131 to the second opening 22, to exit from the second opening 22, to contact the first bridge 2122 with the first back surface 121b, to move across the first bridge 2122, to expose the first sampling surface 121s to the content 140 in the intestinal tract, to load the content 140 on the first sampling surface 121s, to enter the first opening 21, and to carry the loaded content 140 through the sample delivery 12 to the sample depository 141. In a similar fashion, the collector driver 13 is configured to pull the first convoy belt 121 loaded with the sample 140 toward the sample depository 141.

Figure 15:
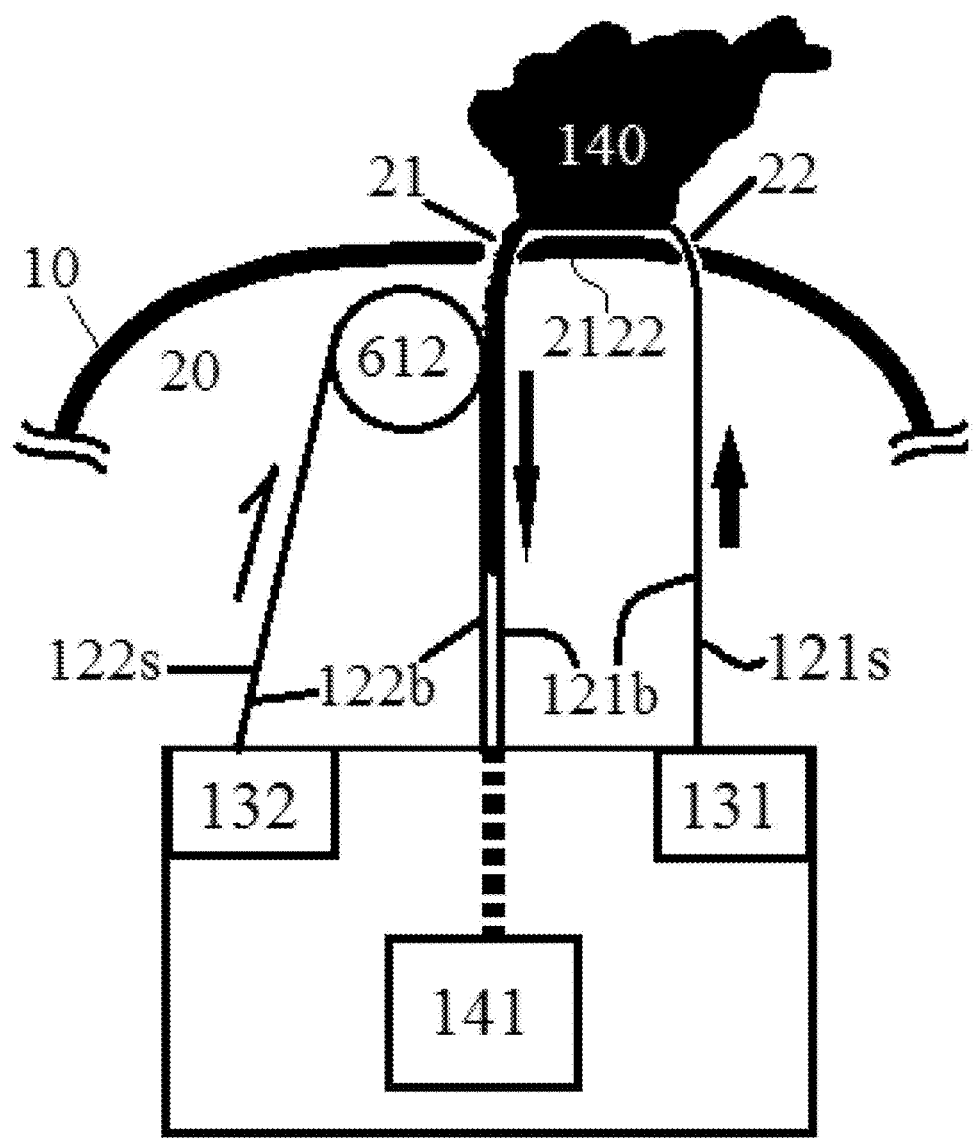
FIG. 15 is a sectional view that schematically depicts a sampling device using two openings on the chamber and a sealing roller in accordance with an exemplary embodiment of the present invention.

The sample collector 11 in the embodiment as shown in FIG. 14 may optionally include a first sealing roller 612 as shown in FIG. 15. Similarly, the sample delivery 12 further comprises a second convoy belt 122 having a second sampling surface 122s and a second back surface 122b. The collector driver 13 further comprises a second belt source 132 for providing the second convoy belt 122 which is blank. In this embodiment, the second convoy belt 122 is configured to extend from the second belt source 132 to the first sealing roller 612, to contact the first sealing roller 612 with the second back surface 122b, to wind around the first sealing roller 612, to cover and seal the passing-by first sampling surface 121s with the second sampling surface 122s, and to move along with the first convoy belt 121 through the sample delivery 12 to the sample depository 141. As a result, the content 140 is sandwiched between the two convoy belts 121 & 122. The collector driver 13 is configured to pull the two convoy belts 121 & 122 loaded with the combined contents 140 at a same speed toward the sample depository 141. Similar to roller 112 in FIGS. 9A and 9B, sealing roller 612 can redirect the movement of the two convoy belts 121 & 122, and therefore press the two convoy belts 121 & 122 together firmly.

Figure 16:
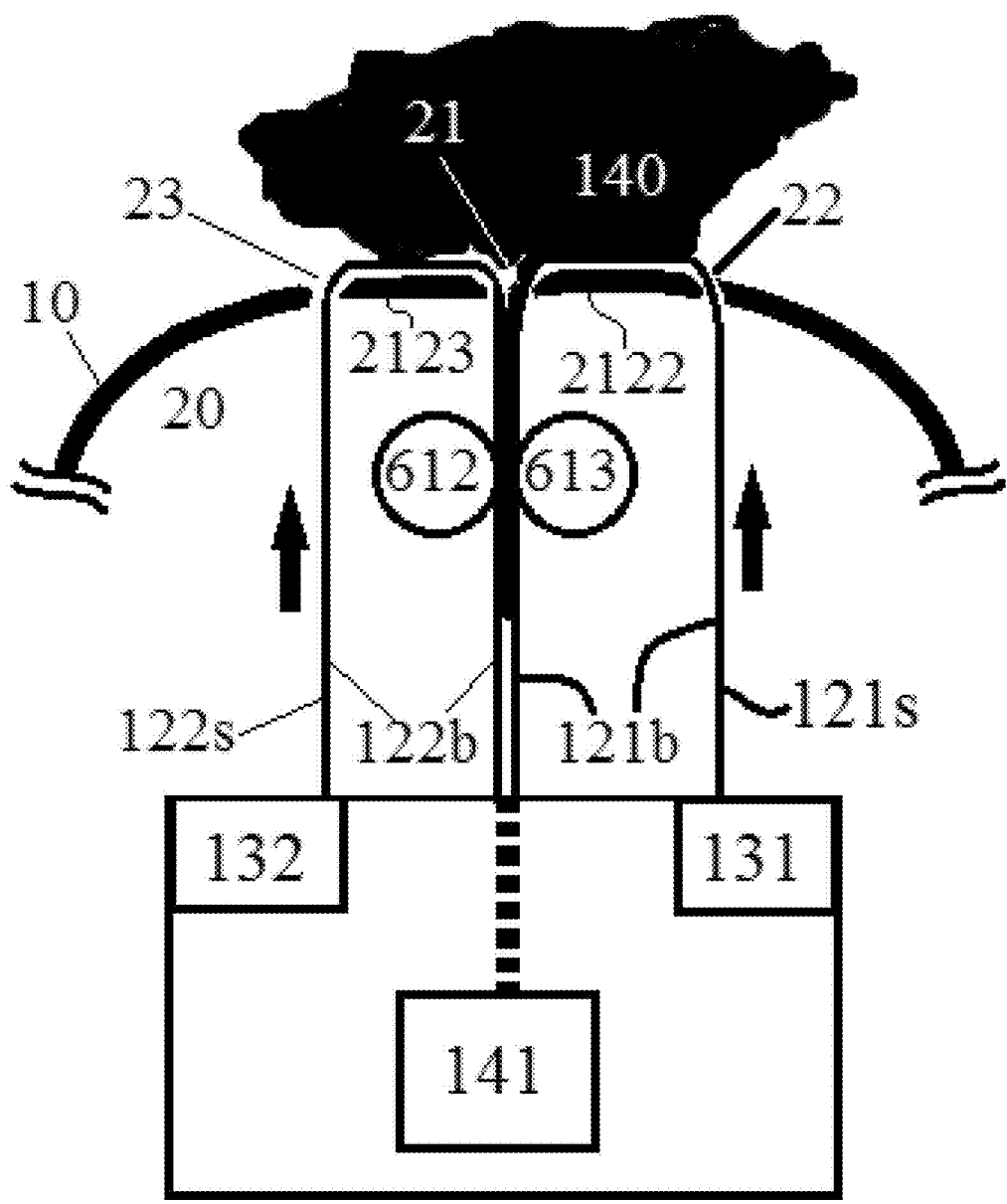
FIG. 16 is a sectional view that schematically depicts a sampling device using three openings on the chamber and two optional sealing rollers in accordance with an exemplary embodiment of the present invention.

The embodiments as shown in FIGS. 7A, 7B and 8 can be modified in any suitable manner. In such a modified embodiment as shown in FIG. 16, the chamber 20 further comprises a second opening 22 and a third opening 23. As such, sample collector 11 comprises a first bridge 2122 formed between the first opening 21 and the second opening 22, and a second bridge 2123 formed between the first opening 21 and the third opening 23. The central positions of openings 21, 22, and 23 may be located on a straight line, or they may constitute a triangle. By the same token, sample delivery 12 comprises a first convoy belt 121 having a first sampling surface 121s and a first back surface 121b, and a second convoy belt 122 having a second sampling surface 122s and a second back surface 122b. Collector driver 13 comprises a first belt source 131 for providing the first convoy belt 121 which is blank, and a second belt source 132 for providing the second convoy belt 122 which is blank. In this embodiment, the first convoy belt 121 is configured to extend from the first belt source 131 to the second opening 22, to exit from the second opening 22, to contact the first bridge 2122 with the first back surface 121b, to move across the first bridge 2122, to expose the first sampling surface 121s to the content 140 in the intestinal tract, to load the content 140 on the first sampling surface 121s, to enter the first opening 21, and to carry the loaded content 140 through the sample delivery 12 to the sample depository 141. Second convoy belt 122 works in a symmetrical way, and is configured to extend from the second belt source 132 to the third opening 23, to exit from the third opening 23, to contact the second bridge 2123 with the second back surface 122b, to move across the second bridge 2123, to expose the second sampling surface 122s to the content 140 in the intestinal tract, to load the content 140 on the second sampling surface 122s, to enter the first opening 21, and to carry the loaded content 140 through the sample delivery 12 to the sample depository 141. The contents 140 loaded on the two convoy belts 121 & 122 are combined when they both pass the first opening 21, and the combined contents 140 are sandwiched between the two convoy belts 121 & 122. The dimension of first opening 21 is preferably so designed that the two convoy belts 121 & 122 are pressed together when they pass through first opening 21. Then, the collector driver 13 pulls the two convoy belts 121 & 122 loaded with the combined contents 140 toward the sample depository 141. In an embodiment, sample collector 11 may further comprise a first sealing roller 612 and/or a second sealing roller 613. When only one sealing roller is present, it should work similarly to roller 112 in FIGS. 9A and 9B, it redirects the movement of the two convoy belts 121 & 122, and therefore press the two convoy belts 121 & 122 together firmly. When two sealing rollers are present, they may redirect the movement of the two convoy belts 121 & 122 and thus press the two belts firmly. Alternatively, they do not redirect the movement of the two convoy belts 121 & 122, but the gap between the two rollers is so configured to press the two belts together firmly.

Figure 17:
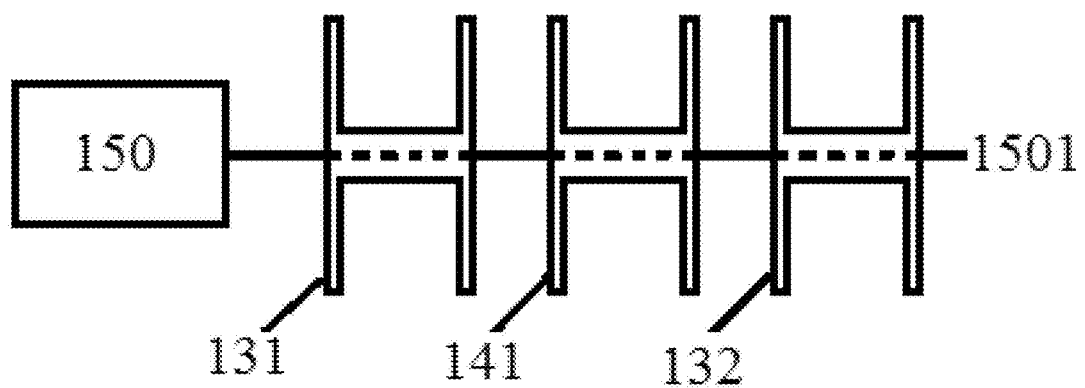
FIG. 17 is a sectional view that schematically depicts the design of a collector driver in accordance with an exemplary embodiment of the present invention.

In a specific embodiment as shown in FIG. 17, a motor 150 rotates a shaft 1501 either clockwise or anticlockwise. First belt source is a roll/reel/spool 131 that is installed around shaft 1501, but it does not engage with the shaft 1501, and is not drivable by the shaft 1501. Therefore, roll/reel/spool 131 can rotate freely around shaft 1501. Second belt source is a roll/reel/spool 132 that is also installed around shaft 1501, but it does not engage with the shaft 1501 either, and is not drivable by the shaft 1501 either. Therefore, roll/reel/spool 132 can rotate freely around shaft 1501. The sample depository may be a collection roll/reel/spool 141 that is installed between 131 and 132 around the shaft 1501. Collection roll/reel/spool 141 does engage with the shaft 1501, and is drivable by the shaft 1501. Therefore, motor 150 can directly rotate collection roll/reel/spool 141, and indirectly rotate rolls/reels/spools 131 and 132 through belts 121 & 122.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A sampling device that can entirely or partially enter into a biological conduit, and can move along the conduit for sampling content contained therein, comprising:
a housing defining a chamber, wherein the chamber has a first opening (or inlet), a sample collector in the chamber that collects the content of the conduit;
a collector driver that drives the sample collector; and
a sample delivery that deliveries the sample collected by the sample collector to the collector driver;
wherein the sample collector comprises a first cylindrical roller and a second cylindrical roller;
wherein the sample delivery comprises a first convoy belt having a first sampling surface and a first back surface, and a second convoy belt having a second sampling surface and a second back surface;
wherein the collector driver comprises a first belt source for providing the first convoy belt which is blank, and a second belt source for providing the second convoy belt which is blank;
wherein the first and the second cylindrical rollers are in parallel with each other;
wherein the first and the second cylindrical rollers have a gap therebetween;
wherein the first convoy belt is configured to extend from the first belt source to the first cylindrical roller, to contact the roller with the first back surface, to wind around the roller, to expose the first sampling surface to the content in the conduit, to load the content on the first sampling surface, to pass through the gap, and to carry the loaded content through the sample delivery to the sample depository;
wherein the second convoy belt is configured to extend from the second belt source to the second cylindrical roller, to contact the roller with the second back surface, to wind around the second cylindrical roller, to expose the second sampling surface to the content in the conduit, to load the content on the second sampling surface, to pass through the gap, and to carry the loaded content through the sample delivery to the sample depository;
wherein the contents loaded, on the first and the second convoy belts are combined when they pass the gap, and the combined contents are sandwiched between the first and the second convoy belts; and
wherein the collector driver is configured to pull the first and the second convoy belts loaded with the combined contents at a same speed toward the sample depository.

2. The sampling device according to claim 1, wherein the sample collector comprises a tongue that pokes out from the housing through the first opening (or inlet) to collect the content in the conduit.

3. The sampling device according to claim 1, wherein the sample collector remains within the housing in its entirety; wherein the first opening (or inlet) receives the content in the conduit; wherein the sample collector collects the content of the conduit that has passed through the first opening.

4. The sampling device according to claim 1, which is a probe, wherein the housing is a flexible tube having a front end with the first opening (or inlet) for inserting into the conduit, and a rear end located outside the conduit; wherein at least a part of the sample delivery is located inside the tube; and wherein the collector driver is located outside the tube near the rear end of the tube.

5. The sampling device according to claim 1, which is a capsule for oral administration or rectal administration, wherein the sample delivery and the collector driver are all located inside the chamber.

6. The sampling device according to claim 1,
wherein
the first cylindrical roller is closer to the first opening than the second cylindrical roller.

7. The sampling device according to claim 6, wherein the first belt source comprises a roll of the first convoy belt around a roller, the second belt source comprises a roll of the second convoy belt around a roller, the sample depository comprises a collection spool or reel around which the two convoy belts sandwiching the content can coil or wrap, and the collector driver further comprises a motor that can rotate the collection spool or reel and pull the two convoy belts sandwiching the content toward the collection spool or reel.

8. The sampling device according to claim 1, wherein the first belt source comprises a roll of the first convoy belt around a roller, the sample depository comprises a collection spool or reel around which the first convoy belt loaded with the sample can coil or wrap, and the collector driver further comprises a motor that can rotate the collection spool or reel and pull the first convoy belt loaded with the sample toward the collection spool or reel.

9. The sampling device according to claim 1, wherein the first belt source comprises a roll of the first convoy belt around a roller, the second belt source comprises a roll of the second convoy belt around a roller, the sample depository comprises a collection spool or reel around which the combined contents sandwiched between the two convoy belts can coil or wrap, and the collector driver further comprises a motor that can rotate the collection spool or reel and pull the combined contents sandwiched between the two convoy belts toward the collection spool or reel.

10. The sampling device according to claim 1, wherein the first or second convoy belt comprises a substrate layer and an adsorbent layer having a sampling Surface, and wherein the adsorbent layer is continuous, homogenous, flat, smooth and free of any indentations and pockets.

11. The sampling device according to claim 10, wherein the adsorbent layer comprises a material selected from form sodium carboxymethylcellulose, polyacrylamide, polyacrylonitrile and acrylic acid polymers, cross-linked acrylic, Karaya gum and polysaccharides.

12. The sampling device according to claim 1, wherein the biological conduit is selected from a human conduit; an animal conduit; intestinal tract or gut; gastrointestinal tract; buccal cavity; pharynx; esophagus; stomach; small intestine; duodenum; jejunum; ileum; large intestine; cecum; colon; rectum; anal canal; respiratory tract; upper respiratory tract; lower respiratory tract; nasal cavity; paranasal sinuses; pharynx; nasopharynx; oropharynx; laryngopharynx; larynx; trachea; primary bronchi; secondary bronchi; tertiary bronchi; bronchioles; lungs; an ear canal; vagina; cervix; uterus or womb; Fallopian tubes; ovaries; urinary tract; kidney; renal pelvis; ureter; urinary bladder; and urethra.

13. A process of sampling a content in a biological conduit comprising:
obtaining the sampling device according to claim 1;
inserting the sampling device entirely or partially into the conduit;
moving the sampling device along the conduit;
collecting the content of the conduit into the sample collector; and
delivering the content collected by the sample collector to the collector driver.

14. The process according to according to claim 13, further comprising continuously loading the content collected from the conduit onto the first or second convoy belt.

15. The process according to according to claim 14, further comprising cutting the first or second convoy belt into pieces for analysis of the content collected from the conduit.

* * * * *